US011921729B1

(12) United States Patent
Shan et al.

(10) Patent No.: US 11,921,729 B1
(45) Date of Patent: Mar. 5, 2024

(54) CONTEXT-AWARE RECOMMENDATIONS IN A HEALTH MANAGEMENT PLATFORM USER INTERFACE

(71) Applicant: Verily Life Sciences LLC, Mountain View, CA (US)

(72) Inventors: Peilun Shan, San Francisco, CA (US); Aurora Adkins, Redwood City, CA (US); Thomas Rudick, San Francisco, CA (US); Lucy Boyd Schachter, Jamaica Plain, MA (US); Bella Powers, Redwood City, CA (US); Nikhil Roy, Sunnyvale, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 1 day.

(21) Appl. No.: 17/219,584

(22) Filed: Mar. 31, 2021

Related U.S. Application Data

(60) Provisional application No. 63/004,280, filed on Apr. 2, 2020.

(51) Int. Cl.
*G06F 16/2457* (2019.01)
*G06F 3/0484* (2022.01)
(Continued)

(52) U.S. Cl.
CPC ........ *G06F 16/24578* (2019.01); *G06F 9/451* (2018.02); *G06F 16/9535* (2019.01);
(Continued)

(58) Field of Classification Search
CPC ............... G06F 16/24578; G06F 9/451; G06F 16/9535; G06F 16/9537; G16H 20/30; G16H 40/67; G16H 20/60
See application file for complete search history.

(56) References Cited

U.S. PATENT DOCUMENTS

2015/0364057 A1* 12/2015 Catani .................... G16H 10/60
434/262
2017/0185250 A1* 6/2017 Cho ....................... G06F 3/0482
(Continued)

FOREIGN PATENT DOCUMENTS

KR          2124249 B1 *  6/2020  ............. G06Q 50/22

OTHER PUBLICATIONS

Google Patents English Language Translation of Kang (Year: 2020).*

*Primary Examiner* — Apu M Mofiz
*Assistant Examiner* — Farhad Agharahimi
(74) *Attorney, Agent, or Firm* — Perkins Coie LLP

(57) ABSTRACT

A technique for generating and presenting context-aware recommendations to assist a patient in managing a chronic health condition. A health management platform provides various services that are accessible to a patient via a graphical user interface (GUI). Input data are received from various services and processed to generate contextual data associated with the patient such as a health state of the patient. Using the contextual data, a recommendation to access a particular service is generated and presented to the patient via the GUI. For example, in response to determining a health state of a patient, a recommendation to access a service to improve the health state of the patient can be automatically presented via the GUI to encourage the patient to access the service.

21 Claims, 14 Drawing Sheets

(51) Int. Cl.
*G06F 9/451* (2018.01)
*G06F 16/9535* (2019.01)
*G06F 16/9537* (2019.01)
*G16H 20/30* (2018.01)
*G16H 20/60* (2018.01)
*G16H 40/67* (2018.01)

(52) U.S. Cl.
CPC ......... *G06F 16/9537* (2019.01); *G16H 20/30* (2018.01); *G16H 20/60* (2018.01); *G16H 40/67* (2018.01); *G06F 3/0484* (2013.01)

(56) References Cited

U.S. PATENT DOCUMENTS

2019/0243944 A1* 8/2019 Jain .................. G16H 80/00
2020/0367807 A1* 11/2020 Lassoued ............. A61B 5/7275
2021/0085240 A1* 3/2021 Pena .................... A61B 5/1116

* cited by examiner

CONTEXT-AWARE RECOMMENDATIONS IN A HEALTH MANAGEMENT PLATFORM USER INTERFACE

CROSS-REFERENCE TO RELATED APPLICATION

This application claims the benefit of U.S. Provisional Application No. 63/004,280, filed Apr. 2, 2020, which is incorporated by reference herein in its entirety.

TECHNICAL FIELD

The disclosed teachings relate to techniques for self-management of chronic health conditions. The disclosed teachings more particularly relate to a graphical user interface associated with a health management platform for assisting a user in self-management of a chronic health condition.

BACKGROUND

Quality of life for patients facing chronic health conditions such as diabetes can be significantly improved through taking active measures to manage such conditions. Active measures for managing a chronic health condition can include, for example, exercise, maintaining a healthy diet, actively monitoring physiological data, taking medications as prescribed, and other measures. Clinical physicians and health coaches can help patients manage chronic health conditions; however, due to infrequent interaction, patients are left to take most active measures on their own.

DETAILED DESCRIPTION

Overview

Figure 1:
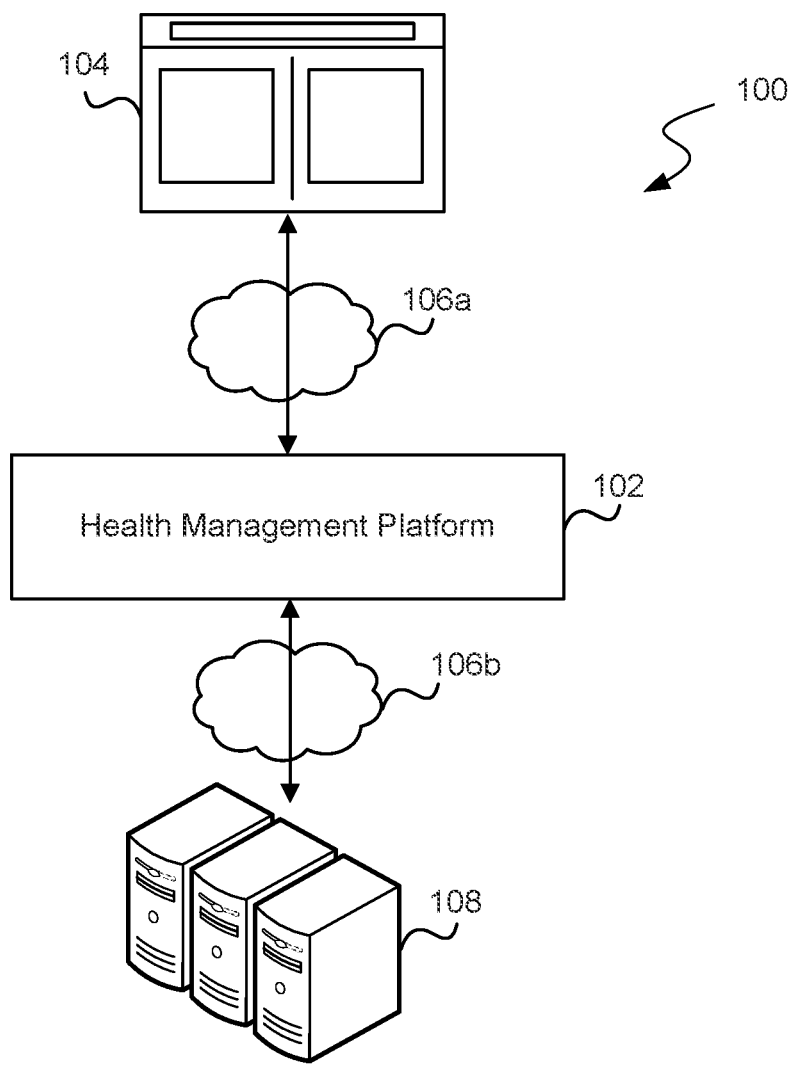
FIG. 1 shows an example network environment that includes a health management platform.

A patient with a chronic health condition such as diabetes may need assistance to help manage his or her chronic health condition. Clinical interactions with patients are infrequent, so it can be difficult for a clinician to follow transitions in the health state of a patient and intervene to assist the patient in managing a chronic health condition. Computer-implemented solutions have been developed to help guide patients with chronic health conditions. Computer-implemented solutions may provide various services that a patient can access to help manage a chronic health condition; however, the patient may not know of and/or know how to effectively utilize the various services.

Introduced here, therefore, is a computer-implemented technique for generating and presenting context-aware recommendations to a patient to assist a patient in managing a chronic health condition. In an example embodiment, a computer-implemented health management platform provides various services such as user-interactive quick actions, curated challenges, educational materials, data tracking and analytics, etc. As used herein, "services" associated with a health management platform may refer to various software-implemented services which are also referred to herein as software as a service (SaaS) services.

A graphical user interface (GUI) associated with the health management platform is displayed at a user computing device through which a patient can access multiple services of the health management platform. Input data are received from various services and processed to generate contextual data associated with the patient such as a health state of the patient or a physical location of the patient. Using the contextual data, a recommendation to access a particular service is generated and presented to the patient via the GUI. For example, in response to generating contextual data indicative of a health state of a patient, a recommendation to access a service to improve the health state of the patient can be automatically surfaced via the GUI to encourage the patient to access the service. By recommending services to the patient based on contextual data, the health management platform can more effectively assist the patient in managing the chronic health condition.

The various SaaS services can "assist" a patient in managing a chronic health condition in various direct and/or indirect ways. Direct assistance in managing a chronic health condition may include, for example, explicit recommendations presented by the virtual sidekick for the patient to perform certain activities (e.g., exercise), eat certain foods (e.g., healthier options), take health measurements (e.g., take blood glucose measurements), consult with health professionals, review educational materials, etc. For example, if the patient needs to exercise more, an SaaS service associated with health management platform can explicitly recommend, through visual and/or audible communication, a particular exercise for the user to perform.

Conversely, indirect assistance may refer to various indirect actions, visual cues, passive interactions, etc. that are tailored to subtly influence a patient's behavior in a certain direction to manage a chronic health condition. For example, in some embodiments, an SaaS service may provide access to a virtual sidekick that is presented via the GUI. The appearance and/or actions by the virtual sidekick can be tailored to build a relationship between the virtual sidekick and the patient thereby increasing the behavioral influence the virtual sidekick has on the patient. In this sense, the virtual sidekick can act as a partner to the patient in the patient's journey to manage his or her chronic health condition.

Terminoloqy

References in this description to "an embodiment" or "one embodiment" mean that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling between two or more elements, either direct or indirect. The coupling/connection can be physical, logical, or a combination thereof. For example, devices may be electrically or communicatively coupled to one another despite not sharing a physical connection.

The term "based on" is also to be construed in an inclusive sense rather than an exclusive or exhaustive sense. Thus, unless otherwise noted, the term "based on" is intended to mean "based at least in part on."

The term "module" refers broadly to software components, hardware components, and/or firmware components. Modules are typically functional components that can generate useful data or other output(s) based on specified input(s). A module may be self-contained. A computer program may include one or more modules. Thus, a computer program may include multiple modules responsible for completing different tasks or a single module responsible for completing all tasks.

When used in reference to a list of multiple items, the word "or" is intended to cover all of the following interpretations: any of the items in the list, all of the items in the list, and any combination of items in the list.

The sequences of operations performed in any of the processes described here are exemplary. However, unless contrary to physical possibility, the operations may be performed in various sequences and combinations. For example, operations could be added to, or removed from, the processes described here. Similarly, operations could be replaced or reordered. Thus, descriptions of any processes are intended to be open-ended.

Technology Overview

FIG. 1 illustrates an example network environment 100 that includes a health management platform 102. A user can interface with the health management platform 102 via an interface 104 to access the services and other functionalities provided by the health management platform 102. The "user" may be any person accessing the health management platform 102 including a patient with a chronic health condition such as diabetes or another person with an interest in the health of the person with the chronic health condition such as a clinician, health coach, etc.

The health management platform 102 may be connected to one or more networks 106a-b. The network(s) 106a-b can include local area networks (LANs), wide area networks (WANs), metropolitan area networks (MANs), cellular networks, the Internet, etc. The health management platform 102 may also communicate with other computing devices over a short-range communication protocol, such as Bluetooth® or Near Field Communication (NFC).

An individual can access various functionalities provided by the health management platform via interface 104. The interface 104 may be accessible via one or more of a web browser, a desktop software program, a mobile application, an over-the-top (OTT) application, or any other type of application configured to present an interface to a user. Accordingly, the interface 104 may be accessed by the user on a user computing device such as a personal computer, tablet computer, personal digital assistant (PDA), mobile phone, game console (e.g., Sony PlayStation® or Microsoft Xbox®), music player (e.g., Apple iPod Touch®), wearable electronic device (e.g., a watch or fitness band), network-connected ("smart") device (e.g., a television or home assistant device), virtual/augmented reality system (e.g., a head-mounted display such as Oculus Rift® and Microsoft HoloLens®), or some other electronic device.

In some embodiments, interface 104 may represent an audio interface through which audible outputs generated by the health management platform 102 (e.g., speech generated by a virtual assistant) are presented to a user and through which audible inputs (e.g., speech by the user) are received from the user. In such embodiments, interface 104 may include or utilize audio input devices such as microphones and audio output devices such as speakers that are integrated with or otherwise communicatively coupled to a user computer device. In some embodiments, interface 104 may additionally include a GUI through which visual outputs are displayed to a user and inputs are received from the user.

In some embodiments, the health management platform 102 is hosted locally. That is, one or more of the computer programs associated with the health management platform 102 may reside on the computing device used to access the interface 104. For example, the health management platform 102 may be embodied as a mobile application executing on a user's mobile phone. In some embodiments, one or more components of the health management platform 102 may be executed by a cloud computing service, for example, operated by Amazon Web Services® (AWS), Google Cloud Platform™, Microsoft Azure®, or a similar technology. In such embodiments, the health management platform 102 may reside on a host computer server that is communicatively coupled to one or more content computer servers 108. The content computer server(s) 108 can include different types of data, user information (e.g., profiles, credentials, and health-related information), and other assets. Additionally, or alternatively, such information could be stored on the host computer server. In some embodiments, one portion of the health management platform 102 may be hosted locally while another portion is hosted remotely (e.g., at a cloud computing service). For example, the health management platform 102 may comprise a mobile application executing locally at mobile device as well as other applications executing at remote host/content servers. In such embodiments, the local and remote portions of the health management platform 102 may communicate with each other via one or more networks 106a-b.

Certain embodiments are described in the context of network-accessible interfaces. However, those skilled in the art will recognize that the interfaces need not necessarily be accessible via a network. For example, a computing device may be configured to execute a self-contained software program that does not require network access. Instead, the self-contained software program may cause necessary assets (e.g., physiological data, healthcare regimen data, processing operations, etc.) to be downloaded at a single point in time or on a periodic basis (e.g., weekly, hourly, or daily).

Figure 2:
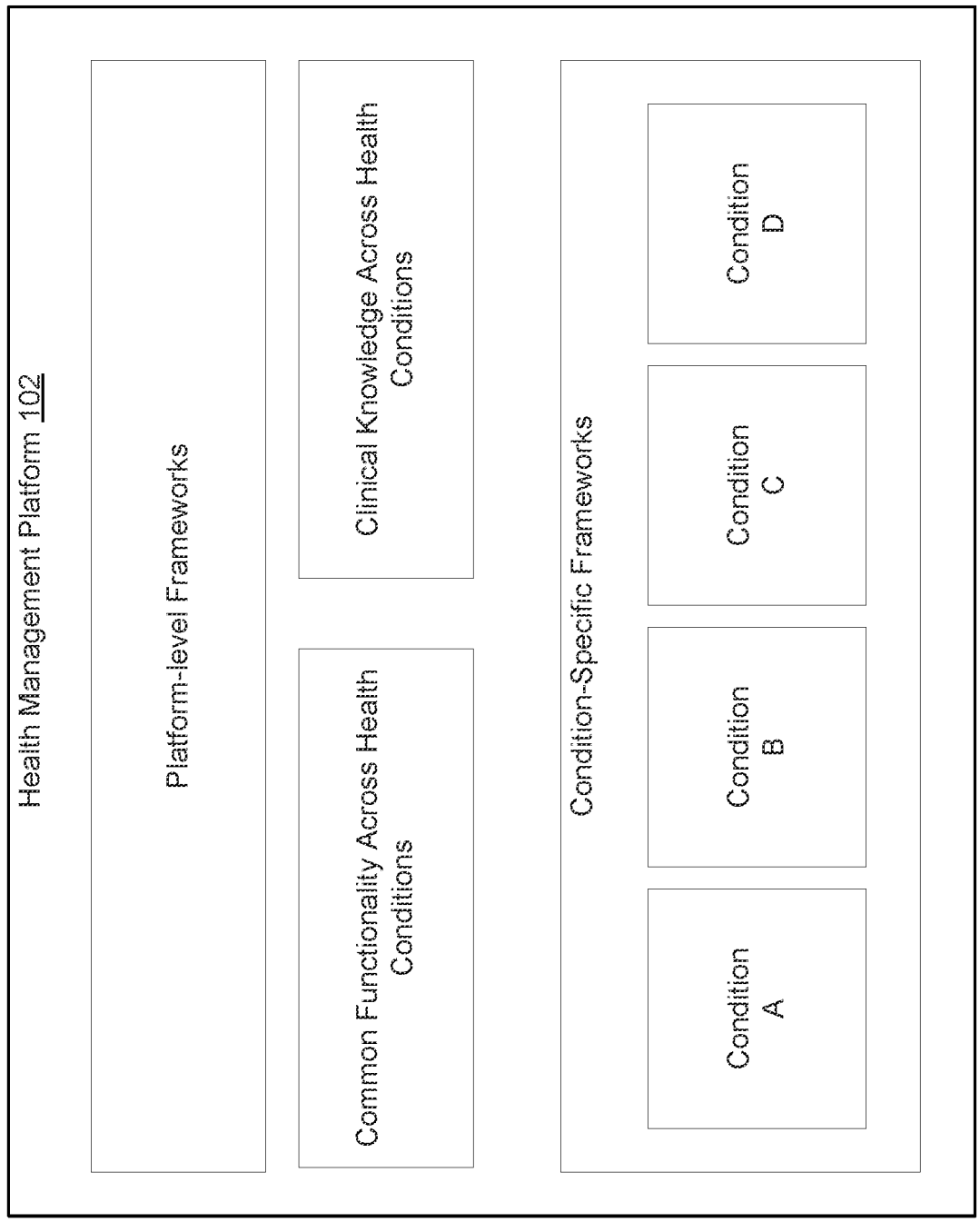
FIG. 2 shows a block diagram of a high-level architecture of an example health management platform.

In some embodiments, a health management platform 102 may be configured to assist users in managing multiple different chronic diseases (also referred to as health conditions). Examples of chronic diseases that may be managed using the health management platform 102 include diabetes, asthma, arthritis, cardiovascular disease, various cancers, etc. FIG. 2 shows a high-level architecture of an example health management platform 102 that depicts an example organization of condition-specific frameworks. As shown in FIG. 2, the health management platform 102 may include multiple different condition-specific frameworks for managing specific chronic health conditions. Each condition-specific framework can be conceptualized as an application that can be run within the broader operating system of the health management platform 102. For example, a user with diabetes may utilize a diabetes-specific application within the health management platform 102 while another user with arthritis may utilize an arthritis-specific application. Each condition-specific framework may include specialized functionality and rely on specialized clinical knowledge associated with the condition. For example, in some embodiments, each condition-specific framework is associated with a different set of one or more computer programs, where each set of one or more computer programs is useable to simulate a virtual assistant to perform audio-based patient surveys that are specifically tailored for a given condition. However, each condition-specific framework may also rely on higher level functionalities and/or clinical knowledge associated with the health management platform 102 that are common across the various different health conditions.

Figure 3:
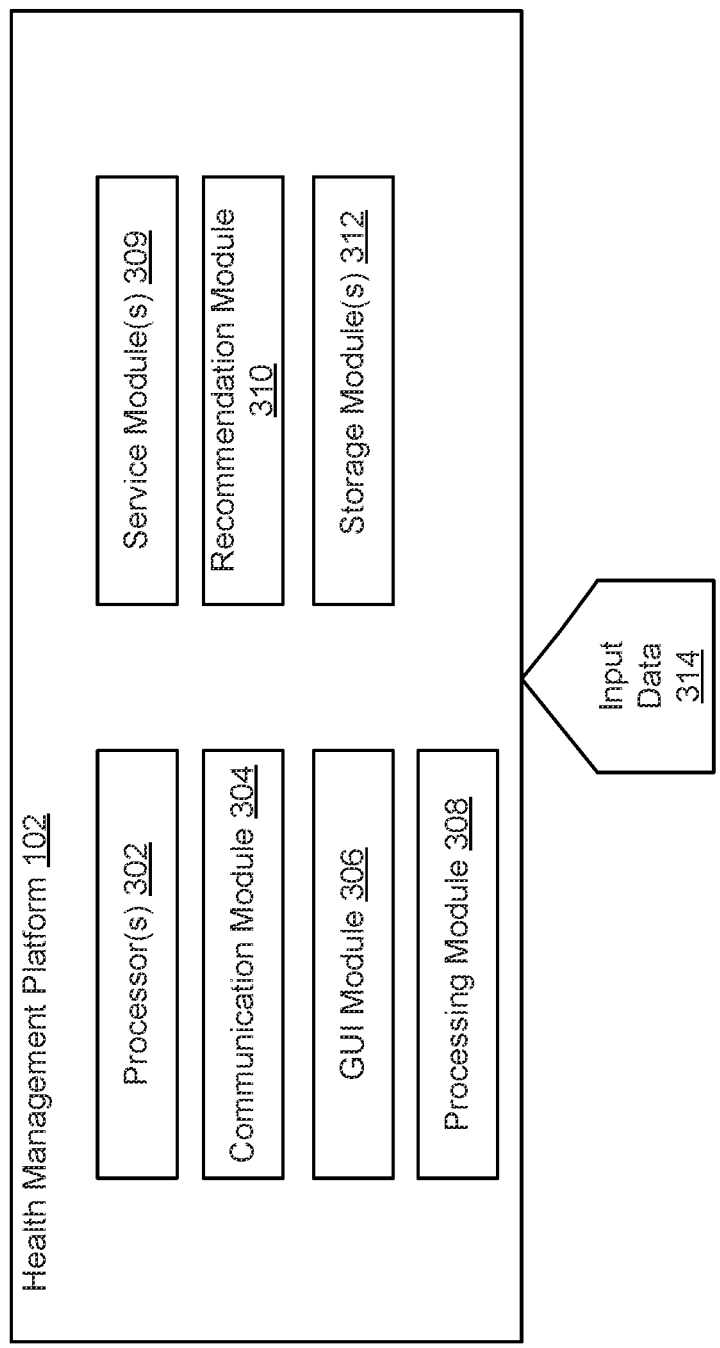
FIG. 3 shows a block diagram of another high-level architecture of an example health management platform.

FIG. 3 shows another high-level architecture of an example health management platform 102. The health management platform 102 can include one or more processors 302, a communication module 304, a GUI module 306, a processing module 308, one or more service modules 309, a recommendation module 310, and one or more storage modules 312. In some embodiments, a single storage module includes multiple computer programs for performing different operations (e.g., format conversion, temporal alignment, statistical analysis), while in other embodiments, each computer program is hosted within a separate storage module. Embodiments of the health management platform 102 may include some or all of these components as well as other components not shown here.

The processor(s) 302 can execute modules (e.g., the processing module 308 and the virtual sidekick module 310) from instructions stored in the storage module(s) 312, which can be any device or mechanism capable of storing information. The communication module 304 can manage communications between various components of the health management platform 102. The communication module 304 can also manage communications between the computing device on which the health management platform 102 resides and another computing device such as a user computing device.

For example, the health management platform 102 may reside on a mobile phone in the form of a mobile application. In such embodiments, the communication module 304 can facilitate communication with a network-accessible computer server responsible for supporting the mobile application. The communication module 304 may facilitate communication with various data sources through the use of application programming interfaces (APIs), bulk data interfaces, etc.

As another example, the health management platform 102 may reside on a server system that includes one or more network-accessible computer servers. In such embodiments, the communication module 304 can communicate with a software program executing on the computing device associated with the individual. Those skilled in the art will recognize that the components of the health management platform 102 can be distributed between the server system and the computing device associated with the individual in various manners. For example, some data may reside on the computing device of the individual, while other data may reside on the server system.

The GUI module 306 can generate GUIs through which an individual can interact with the health management platform 102. For example, a GUI associated with the health management platform 102 may present information to a user to assist a user in managing a chronic health condition and/or may present user interactive elements through which a user can input data, track progress on challenges, access other functionalities, etc.

The processing module 308 can apply one or more operations to input data 314 acquired by the health management platform 102 to provide certain functionalities described herein.

The health management platform 102 may include one or more service modules 309 for providing various services to a user. Services can include, for example, user-interactive quick actions, user-interactive curated challenges, educational materials that are presented via the GUI, data tracking and analytics, virtual sidekicks and/or virtual assistants, audio-based services (e.g., for obtaining patient data), and other types of services. In some embodiments, the one or more service modules 309 in conjunction with the GUI module 306 may present graphical interface elements associated with various services via a GUI of the health management platform. For example, user-interactive quick action tiles may be presented via the GUI to enable the user to access a user-interactive quick action service. The one or more service modules are described in more detail with respect to FIG. 5.

The recommendation module 310 may, in conjunction with the processing module 308, process input data 314 to generate contextual data associated with a user of the health management platform 102. Contextual data may include, for example, data indicative of a chronic health condition of the user (e.g., diabetes, arthritis, etc.), a physical health state of the user, a mood of the user (happy, sad, etc.), an activity performed by the user (e.g., sitting, running etc.), a physical location of the user (e.g., in Charlotte, at home, etc.), a weather condition at a physical location of the user (e.g., sunny, raining, etc.), access by the user of a service of the health management platform, or any other type of information that provides context regarding the user. The recommendation module 310 can use this contextual data to generate recommendations intended to assist the user in managing a chronic health condition. In some embodiments, the generated recommendations can be to access one or more of the services provided by the one or more service modules 309 of the health management platform 102.

Figure 4:
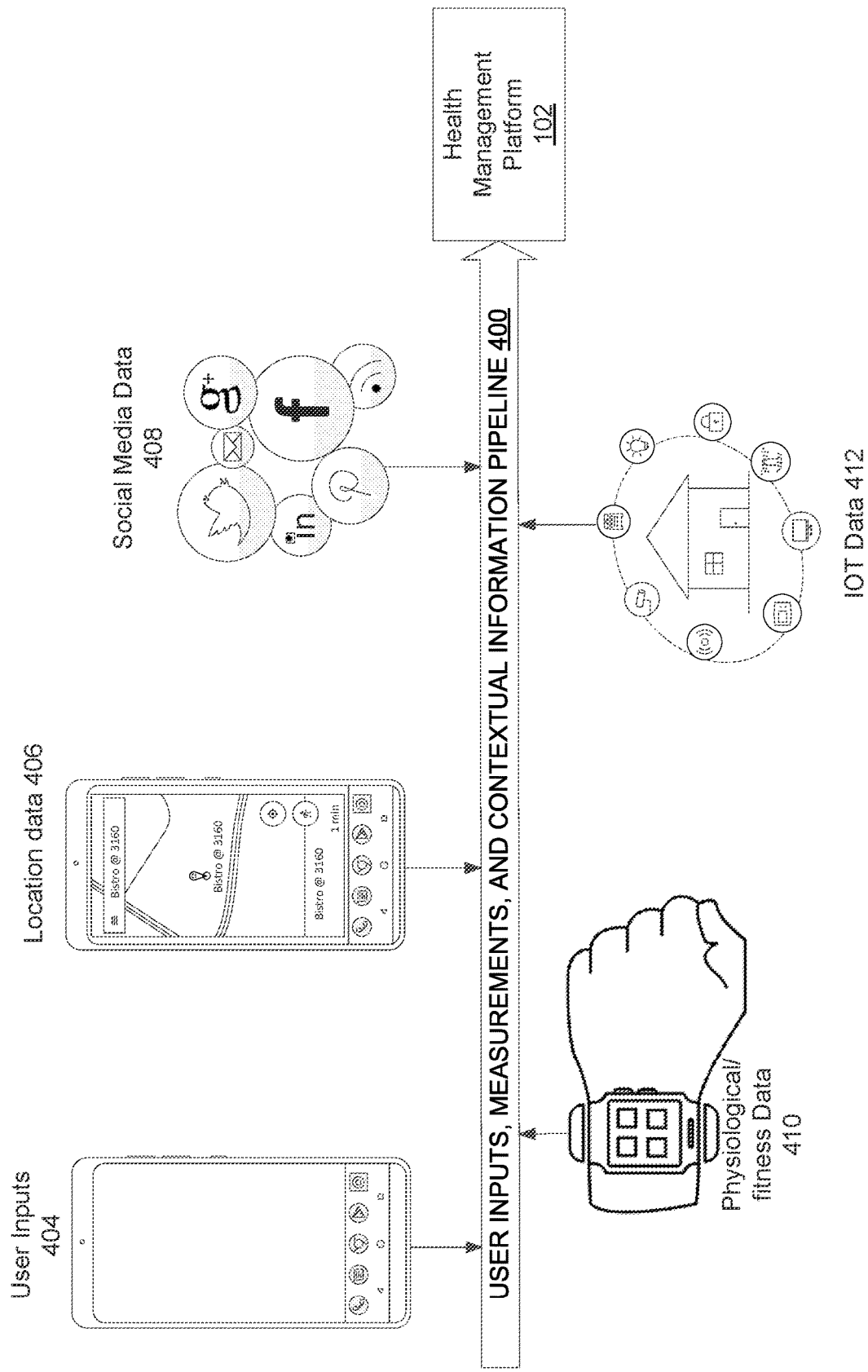
FIG. 4 shows a block diagram illustrating an example data pipeline that may be utilized by a health management platform.

The input data 314 may comprise data from multiple different sources. FIG. 4 shows a block diagram illustrating an example data pipeline 400 comprising user inputs and other contextual data that may be utilized by a health management platform to provide certain functionalities described herein. The data pipeline 400 sources user inputs and/or contextual data from various diverse sources such as user computing devices, health monitoring devices (e.g., fitness trackers, glucometers), other network-connected devices (e.g., Internet of Things (IOT) devices), online services (e.g., location services, social media, etc.), or any other suitable data sources. The data pipeline 400 may feed a health management platform 102 using one or more communication channels (e.g., computer networks 106*a-b*).

User input data 404 may include any data input by the user via the interface 104 associated with the health management platform 102. For example, in some embodiments, user inputs 404 may include audio data that is captured by a microphone at a user computing device. The audio data may include a recorded or live stream capture of a user's voice speaking into the microphone of the user computing device. In some embodiments, user input data may include inputs based on user interaction with a GUI displayed at the user computing device. For example, a user may provide input through touch gestures via a touch screen display and/or may provide input using a separate input device such as a mouse and/or keyboard.

Location data 406 may include a data indicative of a user's physical location and may be determined, for example, using a GPS receiver in a computing device associated with the user. The location information 406 can be used to determine, for example, where the user is located to determine what the weather is like at the user's location. In response to determining a user location, an online weather service can be accessed to determine weather data at the user's location. The location data may also be used to determine, for example, whether the user visited a particular location that may be relevant to the user's chronic health condition such as doctor's office, a restaurant, or a gym. Such location data 406 may be used to, for example, present contextual data alongside a virtual assistant in a GUI.

Social media data 408 may include posts by or related to a patient and made available on social media. For example, a user may take a picture of his or her dinner and post it on Facebook™. The image or related content may be sent over the pipeline 400 to the health management platform 102. The image can be analyzed by the health management platform 102 to determine, for example, if a meal-based goal has been reached, or to trigger presentation of contextual data regarding the user's meal via a GUI, trigger intervention challenges such as meal swap, etc.

Physiological/fitness data 410 may include data regarding a user's health and/or activity. Examples of physiological data include heart rate, blood glucose level, etc. Examples of other fitness-related (but not necessarily physiological) data include a type of exercise performed (e.g., running or jumping), a duration of the exercise (e.g., elapsed time), or other metrics associated with the exercise (e.g., distance traveled).

In some embodiments, physiological data may be acquired from a health monitoring device. For example, a physiological data specifying the blood glucose level of an individual could be generated by a glucose monitoring device. Examples of glucose monitoring devices include continuous glucose monitors (e.g., Medtronic Enlite™ Sensor) and blood glucose meters (e.g., Bayer Contour™).

Similarly, other fitness-related data may be acquired from a fitness tracking device. Examples of fitness tracking devices include mobile phones or smartwatches with motion tracking functionality or specialized fitness trackers such those offered by Fitbit™. A fitness tracking device may track a motion of a user using onboard motions sensors (e.g., one or more accelerometers) and analyze the motion to determine an activity state of the user (e.g., running vs. walking vs. stationary) and one or more fitness-related metrics (e.g., distance traveled, duration of run, calories burned, etc.). In some embodiments, a fitness tracking device may include sensors such as a heart rate monitor configured to generate physiological data such as a heart rate.

In some embodiments, the data pipeline 400 may include IOT data 412 from one or more IOT devices such as smart appliances in the home. For example, IOT data 412 may include data from a smart refrigerator that indicates when a user opens the refrigerator door or a frequency that the user opens the refrigerator door. In other example, data from a smart assistant device (e.g., an Amazon Echo™) can be used to capture audio input from a user. IOT data 412 may include contextual data from any other network-connected devices including environmental sensors, security cameras, network-connected microphones, energy monitoring devices, etc. that can be used to determine information about a state of the user.

In some embodiments, one or more of the data sources associated with the data pipeline 400 may continually upload data to the health management platform 102 so long as the data source remains communicatively coupled to a computer system on which the health management platform 102 resides (e.g., via network connection). In other embodiments, one or more of the data source may periodically upload input data to the health management platform 102 on a periodic basis (e.g., hourly, daily, weekly). In such embodiments, the input data may include multiple data sets for various time intervals (e.g., a first data set for a first time interval, a second data set for a second time interval, etc.). in some embodiments, a computer system associated with the health management platform may actively pull input data from one or more of the data sources (i.e., without requiring that the data sources upload data). In such embodiments, input data may be pulled continually as the data source remains communicatively coupled to a computer system on which the health management platform 102 resides or may be pulled on a periodic basis (e.g., hourly, daily, weekly).

The diagram depicted in FIG. 4 is shown to illustrate the disparate types of input data that can be used by a health management platform; however, not all embodiments will utilize all the data sources shown in FIG. 4. To address privacy concerns associated with the handling of such data, the health management platform 102 is configured to conform with all applicable data privacy and health information laws and regulations. Further, to provide additional safeguards, the health management platform 102 can provide users with options to enable various privacy settings to, for example, specify which input data can be gathered, how such input data can be stored and processed, how the results of the processing of input data (e.g., contextual data) can be stored and used, etc. The privacy settings may also provide users with options to delete data (e.g., certain input data and/or contextual data). Such privacy settings may be adjusted by the user via a GUI associated with the health management platform 102 such as interface 104.

Figure 5:
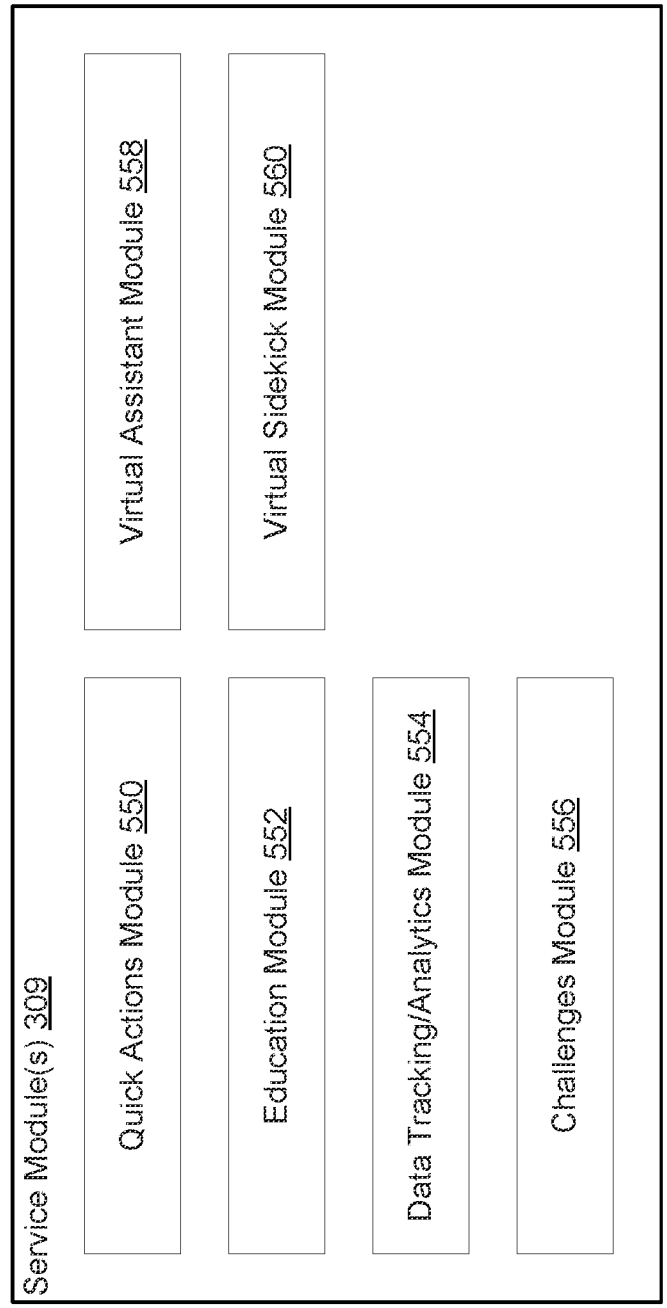
FIG. 5 shows a block diagram of the various service modules of a health management platform.

FIG. 5 shows a block diagram of the multiple service modules 309 associated with a health management platform 102. Specifically, FIG. 5 shows that the service modules 309 may include a quick actions module 550, a challenges module 552, an education module 554, a data tracking module 556, a virtual sidekick module 558, and virtual assistant module 560, although other embodiments may include more fewer service modules than as shown in FIG. 5. As previously mentioned, each of the one or more services may be SaaS services. Accordingly, in some embodiment, each of the one or more service modules depicted in FIG. 5 may represent instructions represented in software (i.e., a computer program or multiple computer programs) that are hosted at one or more computer systems associated with the health management platform 102 and executable to perform various functionalities that are accessible to a user of the health management platform 102 via an interface 104.

The quick actions module 550 handles user-interactive quick actions that can be presented, for example, via a GUI of the health management platform 102. In this context, a "quick action" as a service refers to the presentation of information or interactive elements to a user to cause the user to perform some discrete action or set of actions as well as any analysis or other processing of data associated with the user's performance of such actions. The quick actions presented to the user may be configured to cause the user to perform actions that will improve the overall health of the user. Some example quick actions include taking a health measurement using a device (e.g., a blood glucose meter), logging measured health data, swapping a food item for a healthier option in a meal, logging meal information, ordering a healthy meal, adding an item to a grocery list, refilling a prescription, creating a medication reminder, etc.

As an illustrative example, a user-interactive quick action for taking a health measurement may include an interactive element (e.g., a button) presented via a GUI of the health management platform 102. In response to the user interacting with the element in the GUI, the quick action module 550 may perform various operations including, causing instructions to be presented to the user for taking the measurement, guiding the user (e.g., through audio-based instructions) in taking the measurement, prompting the user to input the acquired measurements, obtaining measurements directly from the measurement device (if communicatively coupled to the health management platform 102), etc. As an illustrative example, a user-interactive quick action for logging a meal may include another interactive element (e.g., a button) presented via the GUI of the health management platform 102. In response to the user interacting with the element in the GUI, the quick action module 550 may perform various operations including prompting the user to input information about the meal (e.g., list of food items, list of ingredients, etc.), prompting the user to take a picture of the meal using a camera device, obtaining an image directly from the camera device (if communicatively coupled to the health management platform 102), processing the image to identify information about the meal (e.g., list of food items, list of ingredients, etc.), analyzing the information about the meal to estimate nutritional information, etc. These are just examples, of some user-interactive quick actions that may be implemented as a service using the quick actions module 550.

The education module 552 handles the presentation of educational materials to a user, for example, via a GUI of the health management platform 102. Educational materials can be presented using various different media including text, images, video, etc. In some embodiments, the education module 552 generates educational tiles including one or more educational media from various sources and presents the educational tiles in the GUI. In some embodiments, the educational tiles may be in the form of interactive elements presented in the GUI. User interaction with an educational tile may cause the educational media to be displayed to the user via the GUI or may link the user to another source (e.g., a webpage or another app) to view the media. In some embodiments, the education module 552 will generate educational materials (e.g., educational tiles in the GUI) based on input data associated with the user. For example, the education module 552 may determine, based on input data, that the user has diabetes and generate and present one or more educational tiles that specifically provide information regarding diabetes. Categories of educational tiles include, general health education, specific disease education, mindfulness education, nutritional education, financial education (e.g., for budgeting), step-by-step tutorials (e.g., for administering medication, using health measurement devices, or using the health management platform), information regarding local services (e.g., local health care providers, local support groups), information regarding the health management platform, specific insights (e.g., effects of swapping food items on blood glucose levels), etc.

The data tracking and analytics module 554 handles the tracking and analysis of various patient data such as physiological data or fitness data. For example, in the case of a user with diabetes, the data tracking and analytics module 554 may track blood glucose levels for the user over time based on user provided inputs (e.g., via text or audio-based patient surveys) and/or based on inputs received directly from a connected blood glucose meter. The data tracking and analytics module 554 may further process the tracked patient data to generate analytics (e.g., various aggregated statistics) and/or generate visualizations to interpret and communicate the data to the user.

The challenges module 556 handles user-interactive challenges that can be presented, for example, via a GUI of the health management platform 102. In this context, a "challenge" as a service refers to the presentation of information or interactive elements to a user to cause the user to perform a series of actions towards some challenge goal as well as any analysis or other processing of data associated with the user's performance of challenge-related actions. In contrast with a quick action, a challenge may involve a sequence of multiple different operations over some period of time (e.g., a week) that are configured to cause a user to perform various actions towards a challenge goal. As with the quick actions, challenges presented to the user may be configured to cause the user to perform actions that will improve the overall health of the user. Some example challenges include hitting a target blood glucose level, swapping out a carbohydrate-heavy food item in each meal for a week, exercising at least 1 hour every day for a week, going to bed a particular time every night for a week, etc.

In some embodiments, the challenges module 556 coordinates with other services modules (e.g., quick actions module 550, education module 554, and data tracking/analytics module 554) to surface various services to a user via the GUI throughout a challenge period. As an illustrative example, if the user elects to participate in a challenge to maintain a target average blood glucose level for a week, the challenges module 556, working independently or in conjunction with other modules, may surface various services such as quick actions (e.g., take a blood glucose reading), educational tiles (e.g., learn about blood glucose levels), data tracking and analytics (e.g., a chart of tracked blood glucose levels), etc. during the week to assist the user in achieving the target average blood glucose level.

In some embodiments, challenges implemented by the challenges module 556 are curated by other human users. For example, another user of the health management platform 102 with expertise in a chronic health condition (e.g., a clinician or health coach) may curate a challenge by selecting multiple services and designating timing or other conditions to surface the services as part of the challenge. In other embodiments, challenges are generated automatically by the challenges module 556 using, for example, various rules or machine learning techniques.

The virtual assistant module 558 handles simulating and presenting a virtual assistant to a user. The simulated virtual assistant may be presented, via a GUI, to assist the user in various ways to help manage a chronic health condition. For example, in some embodiments, a virtual assistant can be implemented to participate in text-based or audio-based natural language conversations with the user to obtain patient data or provide other assistance. The virtual assistant may be configured to present text-based messages via a messaging interface such as email, SMS, etc. Alternatively, or in addition, the virtual assistant may be configured to generate audible natural language messages (i.e., spoken messages) and present those messages via an audio output device (e.g., a speaker) of a user computing device. Similarly, the virtual assistant may be configured to receive user text-based messages via a messaging interface. Alternatively, or in addition, the virtual assistant may be configured to receive audio data that was captured using an audio input device (e.g., microphone) at the user computing device, process the audio data, and interpret the audio data as a natural language message by the user. For example, in some embodiments, a virtual assistant may use speech recognition processing to identify a string of words included in audio data received from a user computing device. The virtual assistant may further parse the string of words and apply natural language processing (NLP) to interpret meaning from the string of words indicated in the audio data. The virtual assistant may then, based on the interpreted meaning of the user's message, generate another natural language message as part of the simulated conversation.

The virtual sidekick assistant module 558 may comprise one or more computer programs operable to simulate the virtual assistant to take part in natural language conversations with a user, for example, to obtain patient data. In some embodiments, the virtual assistant may be implemented in the form of a chat bot that is configured to generate and present outputs in the form of natural language messages to a user and receive and process natural language replies from a user as part of a natural language conversation. In some embodiments, the virtual assistant may rely on pre-scripted user interactions. For example, the virtual assistant module 558 may include a database of pre-scripted reply templates that can be selected from and/or selectively modified based on interpreted messages received from a user. In some embodiments, the virtual assistant may utilize more advanced artificial intelligence techniques. For example, virtual assistant module 558 may include one or more machine learning models that are configured to process input user messages to interpret those messages and generate natural language replies to the user messages.

The virtual sidekick module 560 handles simulating and presenting a virtual sidekick to a user. The simulated virtual sidekick may be presented, via a GUI, as a partner or peer to a user to assist the user in managing a chronic health condition such as diabetes. In some embodiments, to enhance the partner or peer relationship between the virtual sidekick and the user, the virtual sidekick may be depicted as facing the same challenges as the user. For example, if the user has a chronic health condition, the virtual sidekick may be depicted, through actions and/or appearance, as having the same, or a substantially similar, chronic health condition. In contrast with a virtual assistant, the virtual sidekick is not intended to serve as an authority or expert to the user. The virtual sidekick is instead intended to share the experience with the user of managing the user's chronic health condition. For example, the mood or health condition of the virtual sidekick may be adjusted to correspond to a detected mood or health condition of the user. As another example, the virtual sidekick may be depicted as performing certain activities associated with the management of a chronic health condition such as exercising, making dietary changes, taking health monitoring measurements, etc. Further, the virtual sidekick may be presented as fallible to enable the user to relate to the virtual sidekick. For example, the virtual sidekick may be depicted as making a mistake while taking a blood glucose reading using a glucose monitoring device. In this sense, successes and failures by the user may correspond to successes and failures by the virtual sidekick, and vice versa.

The virtual sidekick module 560 may comprise one or more computer programs operable to simulate the virtual sidekick. In some embodiments, such computer programs may include instructions for performing one or more predefined interaction scripts in response to detected events or conditions. For example, instructions associated with a computer program may cause a visual representation of the virtual sidekick to depict the virtual sidekick performing a predefined action (e.g., walking) in response to detecting, based on input data, a condition or event (e.g., the user walking). Alternatively, or in addition, the computer program used to simulate the virtual sidekick may include or utilize one or more artificial intelligence models. In such embodiments, input data (and/or contextual data) may be fed into an artificial intelligence model that generates outputs that cause the presentation of the virtual sidekick in the GUI to dynamically update.

Context-Aware Recommendations

Figure 6A:
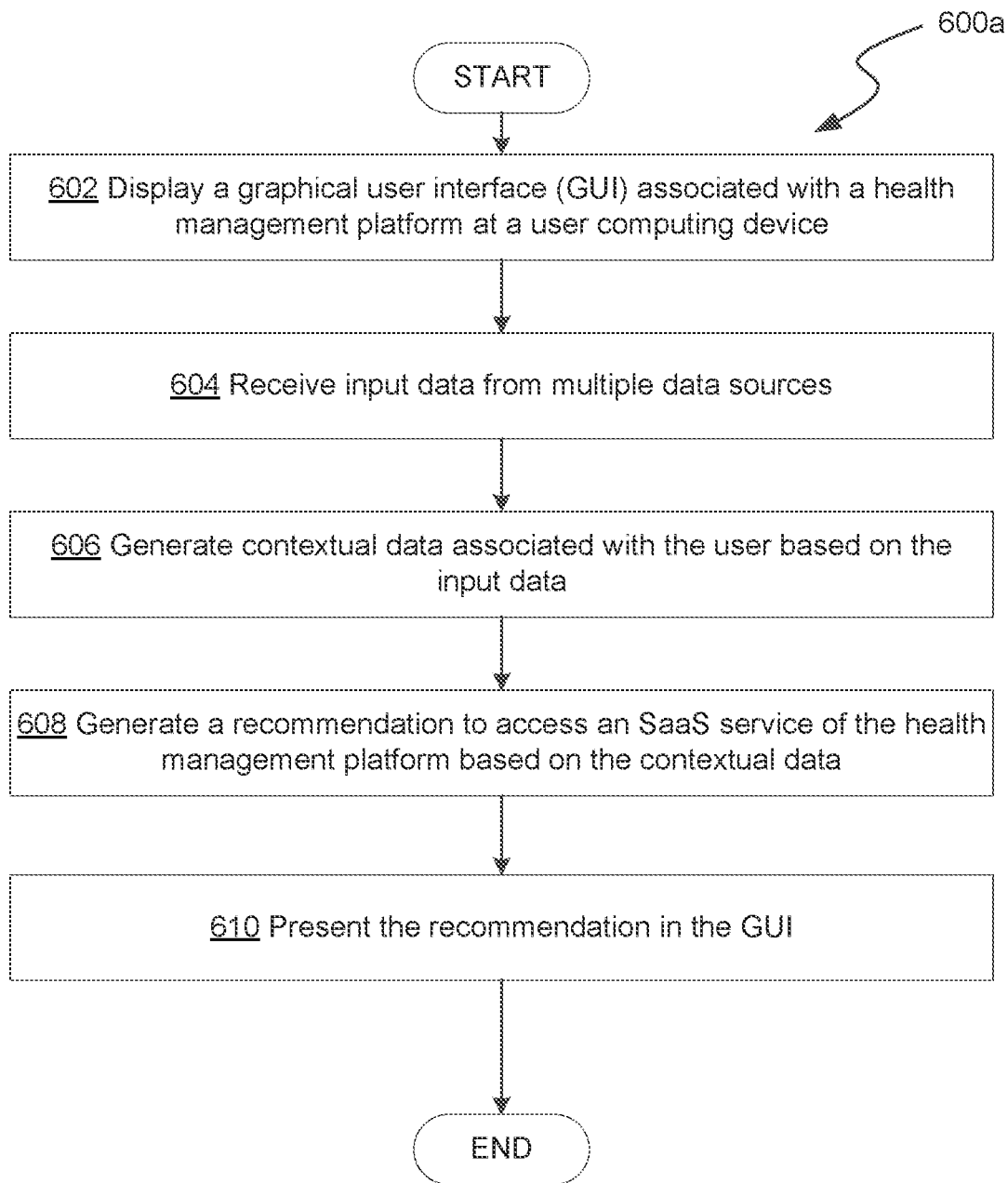
FIG. 6A shows a flow diagram of an example process for generating a presenting context-aware recommendations in a graphical user interface (GUI) of a health management platform.

FIG. 6A shows a flow diagram of an example process 600a for presenting context-aware recommendations in a GUI of a health management platform 102.

Example process 600a begins at operation 602 with displaying a GUI associated with a health management platform at a user computing device. For example, as described with respect to FIG. 1, an individual user (e.g., a patient with a chronic health condition) may access various functionalities of a health management platform 102 using interface 104. Interface 104 may include a GUI that is displayed at a user computing device using any type of application configured to present a GUI.

Example process 600a continues at operation 604 with receiving input data from multiple different data sources. For example, as described with respect to FIG. 4, various input data may be received by one or more computer systems associated with a health management platform 102 via a data pipeline 400. The input data may include, for example, user inputs via the GUI presented at operation 602, location data received from the user computing device, weather data received from a weather service, social media data received from one or more social media platforms, physiological data received from a health monitoring device, fitness data received from a fitness tracking device, IOT data received from various network connected devices around the user's home, and various other types of data.

Example process 600a continues at operation 606 with generating contextual data associated with the user based on the input data. In other words, operation 606 may include processing raw input data received from the multiple data sources to learn, infer, identify, or otherwise determine some type of understanding of the context of the user. As previously discussed, contextual data may include, for example, data indicative of a chronic health condition of the user (e.g., diabetes, arthritis, etc.), a physical health state of the user, a mood of the user (happy, sad, etc.), an activity performed by the user (e.g., sitting, running etc.), a physical location of the user (e.g., in Charlotte, at home, etc.), a weather condition at a physical location of the user (e.g., sunny, raining, etc.), access by the user of a service of the health management platform, or any other type of information that provides context regarding the user.

In some embodiments, operation 606 may include processing input data received at operation 604 to determine a health state of the user. The term "health state" can refer to physical health, mental health, emotional health, or any combination thereof. Input data used to determine the physical and/or mental health state of the user may include, for example, user inputs received via the GUI, physiological data received from a health monitoring device, fitness data received from a fitness tracking device, social media data including posts by the user, etc.

As an illustrative example, a physical health state for a diabetic user may include a glycemic state determined based on measured blood glucose levels received from a glucose monitoring device. In such an example, the health state may be defined categorically (e.g. low, normal, high, etc.) or in any other appropriate manner.

As another illustrative example, a mental or emotional state for a user may be determined by analyzing sensor inputs from a camera and/or microphone of the user computing device. For example, images of the user captured by a camera may be analyzed to identify features indicative of a defined mental or emotional state. Similarly, recordings of the user's voice captured by a microphone may be analyzed to identify features indicative of a defined mental or emotional state. Identified features used to determine a health state of the user may include linguistic features, non-linguistic features, and/or paralinguistic features. Linguistic features refer to aspects of spoken communication that involve words. Examples of linguistic features include the word count of different n-grams, whether jargon/slang is used, etc. Paralinguistic features refer to those aspects of communication that do not involve speech. Paralinguistic features often add emphasis or shades of meaning to what an individual says. Examples of paralinguistic features may include body language, gestures, facial expressions, micro expressions, etc. Non-linguistic features also refer to those aspects of spoken communication that do not involve words. Much like paralinguistic features, non-linguistic features can add emphasis or shades of meaning to what an individual says. Examples of non-linguistic features include tone, pitch, volume/loudness, speaking rate, shimmer, jitter, etc.

As another illustrative example, an activity of the user may be determined by analyzing sensor inputs from a user computing device and or a fitness tracking device. For example, operation 606 may include analyzing images from a camera, motion data from an accelerometer, heart rate data from a heart rate sensor, or any combination thereof to detect motion by the user and or a level of physical exertion and thereby infer or otherwise determine a type of activity performed by the user (e.g., standing still, walking, running, jumping, etc.).

As another illustrative example, a physical location of the user may be determined by analyzing location data, for example, received from the user computing device. For example, the user computing device may transmit GPS coordinates to a computer system of the health management platform 102. Location data (e.g., in the form of GPS coordinates) may be used to identify a physical locale or landmark corresponding to the user's exact physical location. For example, using received GPS coordinates, the system may determine that the user is in a particular city (e.g., Charlotte), in a particular neighborhood, at a particular physical address, at a particular type of location (e.g., at home, a gym, or a doctor's office), etc.

As another illustrative example, a weather condition at the physical location of the user may be determined by analyzing location data of the user and cross referencing to weather data from an online weather service. For example, in response to receiving location data (e.g., in the form or GPS coordinates), the system may access an online weather service to determine a weather condition (e.g., sunny, raining, etc.) at a physical location corresponding the received location data.

In some embodiments, operation 606 may include processing received input data using one or more rules to generate the contextual data associated with the user. For example, a rule may specify that a user's location is at home if received GPS coordinates are within a threshold distance of a user's known home address. As another example, a rule may specify that a user's physical health state is normal if blood glucose levels received from a glucose monitoring device are within a predefined range. These are just some illustrative examples of rules that may be applied to generate contextual data based on received input data.

In some embodiments, operation 606 may include processing received input data using one or more machine learning models to generate the contextual data associated with the user. For example, a machine learning model may be trained to infer a physical health state of a user based on input physiological data. As another example, a machine learning model may be trained to infer an activity performed by a user based on input motion data and physiological data. In any case, the one or more machine learning models may apply one or more different processes to the data using various machine learning techniques such as decision trees, Naïve Bayes classifiers, support vector machines, random forests, artificial neural networks, etc.

Example process 600 continues at operation 608 with generating a recommendation based on the contextual data generated at operation 606. In some embodiments, operation 608 may specifically include generating a recommendation to access one of the multiple services of the health management platform 102. In some embodiments, the recommendation is generated to improve the overall health of the user. In other words, operation 608 may include selecting a particular service from multiple services of the health management platform 102 that is likely to improve the overall health of the user given the contextual data associated with the user. For example, if the user is feeling ill and has diabetes, the recommendation may be to access a quick action service to take an updated blood glucose reading. As another example, if the user is in physical proximity to a pharmacy and has a prescription that has not been filled, the recommendation may be to access a quick action service to fill and pick up the prescription at the pharmacy. As another example, if the user was recently diagnosed with diabetes, the recommendation may be to access an educational materials service to learn more about diabetes. As another example, if the user previously accessed a quick action service to perform an exercise activity, the recommendation may be to access a challenge service to set and work towards a particular exercise goal.

In some embodiments, the contextual data generated at operation 606 may include data indicative of a health state of the user. In such cases, generating the recommendation at operation 608 may include identifying a predefined activity that is known or likely to improve the health state of the user and generating a recommendation to access a particular service that will cause the user to perform the predefined activity. The type of predefined activity will differ depending on the type of health state of the user and the type of chronic health condition of the user. Examples of predefined activities that may improve the health state of the user include, using a health monitoring device to acquire updated phycological data, performing a fitness activity (i.e., exercising), performing a food swap activity (i.e., swapping a food item for a healthier alternative), consulting a health expert (e.g., calling or visiting a doctor), taking a medication, performing a mindfulness activity (e.g., meditating), etc.

In some embodiments, the recommendation to access the particular service may be generated in response to determining that a likelihood that the service causes the user to perform the predefined activity satisfies a likelihood criterion. For example, the likelihood criterion may be satisfied if the particular service is more likely than all the other services of the health management platform 102 to cause the user to perform the predefined activity. As another example, the likelihood criterion may be satisfied if the likelihood is above a specified threshold. In any case, the likelihood that a particular services may cause a user to perform a predefined activity may be based on historical data collected regarding behavior patterns of the user and/or other users of the health management platform 102 taking into consideration contextual data regarding such users.

In some embodiments, the contextual data generated at operation 606 may include data indicative of a physical location of the user. In such cases, operation 608 may additionally include determining that an identified predefined activity can be performed by the user at or in proximity to the physical location of the user. For example, if the predefined activity intended to improve the health state of the user is swimming, operation 608 may additionally include determining that a physical location of the user (as indicated in the contextual data) is at or in proximity to a body of water or swimming pool in which the user can swim. As another example, if the predefined activity intended to improve the health state of the user is taking a blood glucose measurement, operation 608 may additionally include determining that a physical location of the user (as indicated in the contextual data) is at or in proximity to the user's home or at or in proximity to a physical location of a blood glucose monitoring device.

In some embodiments, the contextual data generated at operation 606 may include information indicative of a current or recent activity by the user. In such cases, operation 608 may additionally include determining that an identified predefined activity is related to or otherwise associated with the current or recent activity by the user. For example, if the current or recent activity by the user is eating a meal, a selected predefined activity to improve the health state of the user may include swapping a first food item in the meal for a healthier second food item since those activities are related. As another example, if the current or recent activity by the user is exercising, a selected predefined activity to improve the health state of the user may include meeting an exercise goal. As another example, if the current or recent activity by the user is using a health monitoring device to acquire updated physiological data, a selected predefined activity to improve the health state of the user may include entering the updated physiological data via the GUI.

Figure 7:
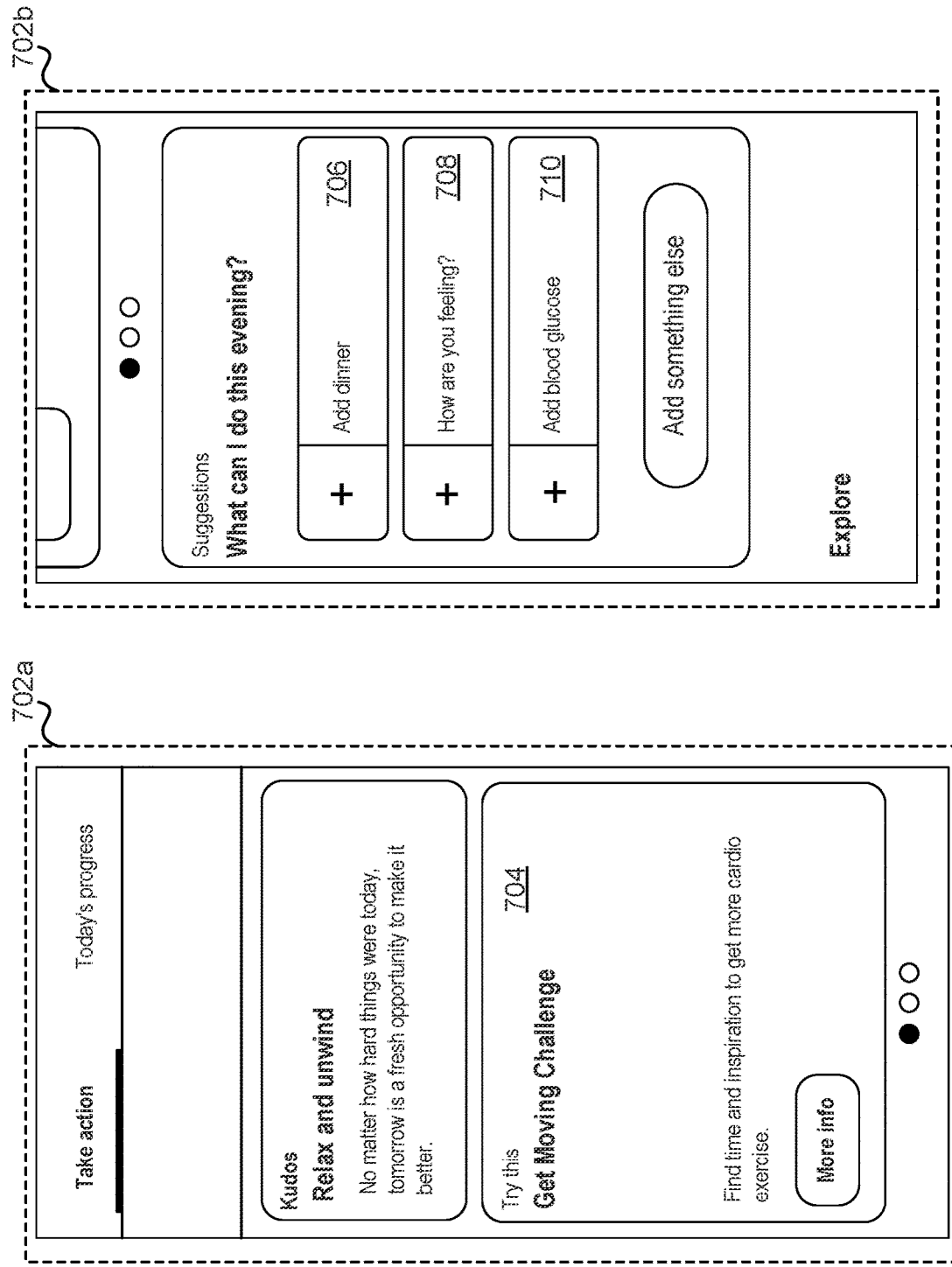
FIGS. 7-9 shows screens of an example GUI of a health management platform.
Figure 8:
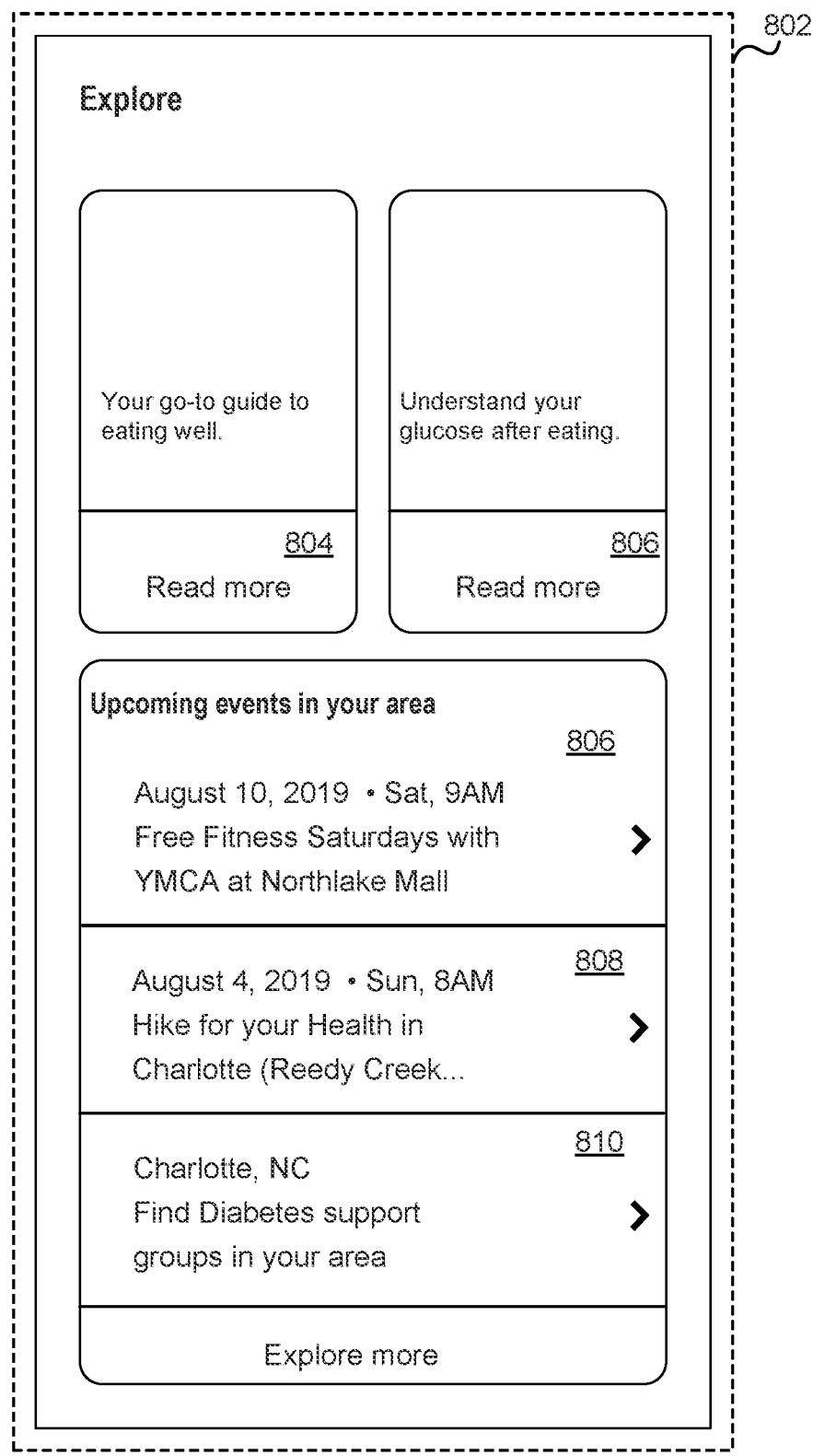
Figure 9:
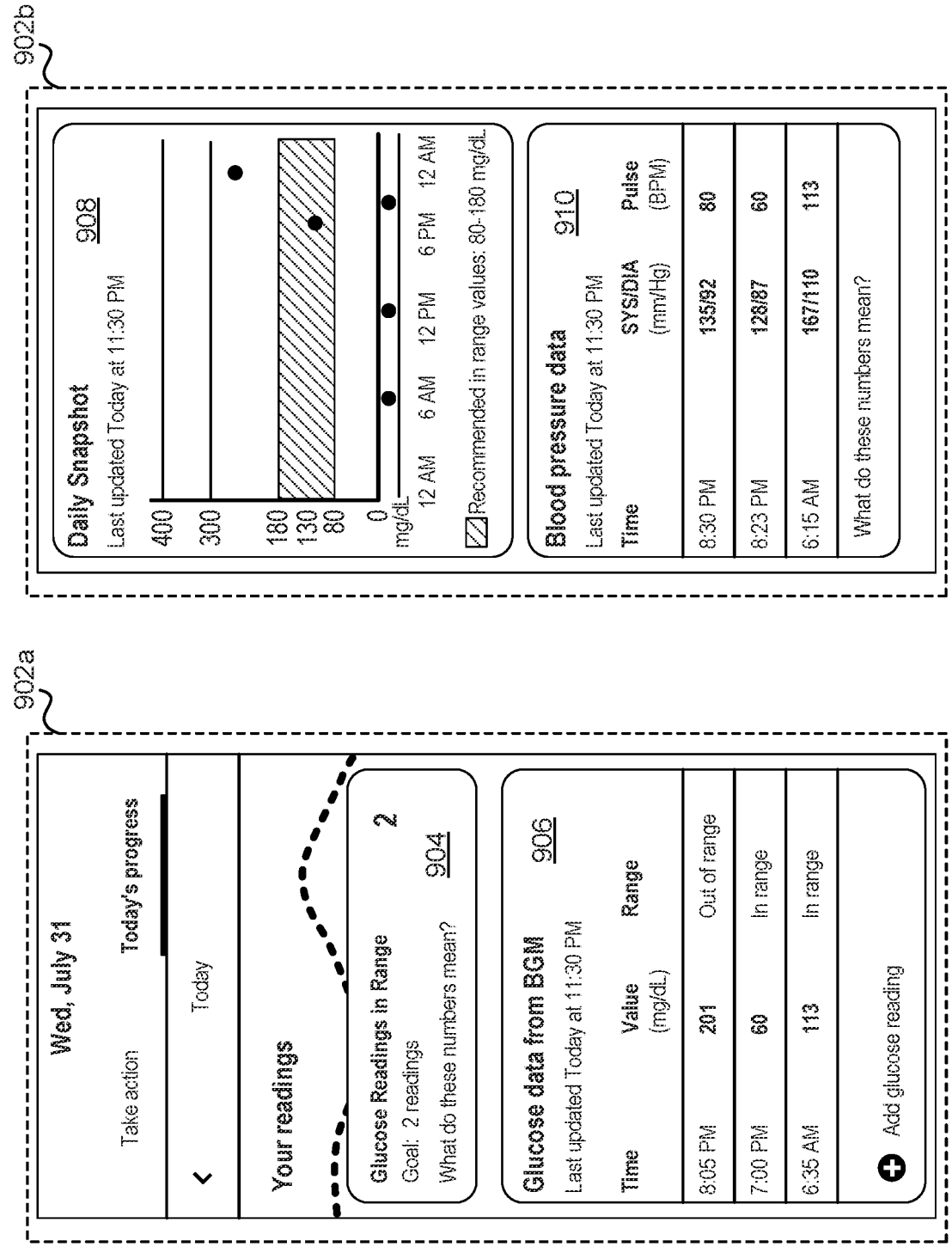

Example process 600a concludes at operation 610 with presenting the recommendation generated at operation 608. In some embodiments, the recommendation may be presented as an audible output via a speaker associated with a user computing device. In other embodiments, the recommendation may be presented visually via a GUI of the health management platform 102. For example, in such embodiments, operation 610 may include presenting, in the GUI, an interactive element through which the user can access the recommended service. In other words, operation 610 may include, generating the interactive element and displaying the generated interactive element in the GUI. Interactive elements may include, for example, buttons, editable fields, checkboxes, radio buttons, interactive lists, toggles, etc. Some examples of interactive elements corresponding to recommended services are shown in FIGS. 7-9.

In some embodiments, operations 608 and 610 may be performed in real time or near real time (i.e., within seconds or fractions of a second) with operation 606. In other words, a recommendation to access a service may be generated and displayed in the GUI in real time or near real time in response to generating the contextual data associated with the user. Further, new recommendations may be generated as new input data are received and the contextual data associated with the user changes. In other words, although not shown in FIG. 6, example process 600 may additionally include receiving updated input data from one or more of the multiple data sources (similar to operation 604), detecting a change in the contextual data associated with the user as the updated input data are received from the one or more of the plurality of data sources (similar to operation 606), generating, in response to the detected change in the contextual data, a new recommendation to access another service of the multiple services of the health management platform 102 (similar to operation 608), and presenting the new recommendation to the user (similar to operation 610). In some embodiments, an interactive element associated with a new recommendation may replace another interactive element associated with a previous recommendation. For example, an interactive element that links a user to a first service may dynamically update to link the user to a second service in response to determining updated contextual data associated with the user. Alternatively, or in addition, an interactive element associated with a new recommendation may supplement another interactive element associated with a previous recommendation. For example, a first interactive element that links a user to a first service may be presented, the GUI, along with a second interactive element that links the user to a second service.

Figure 6B:
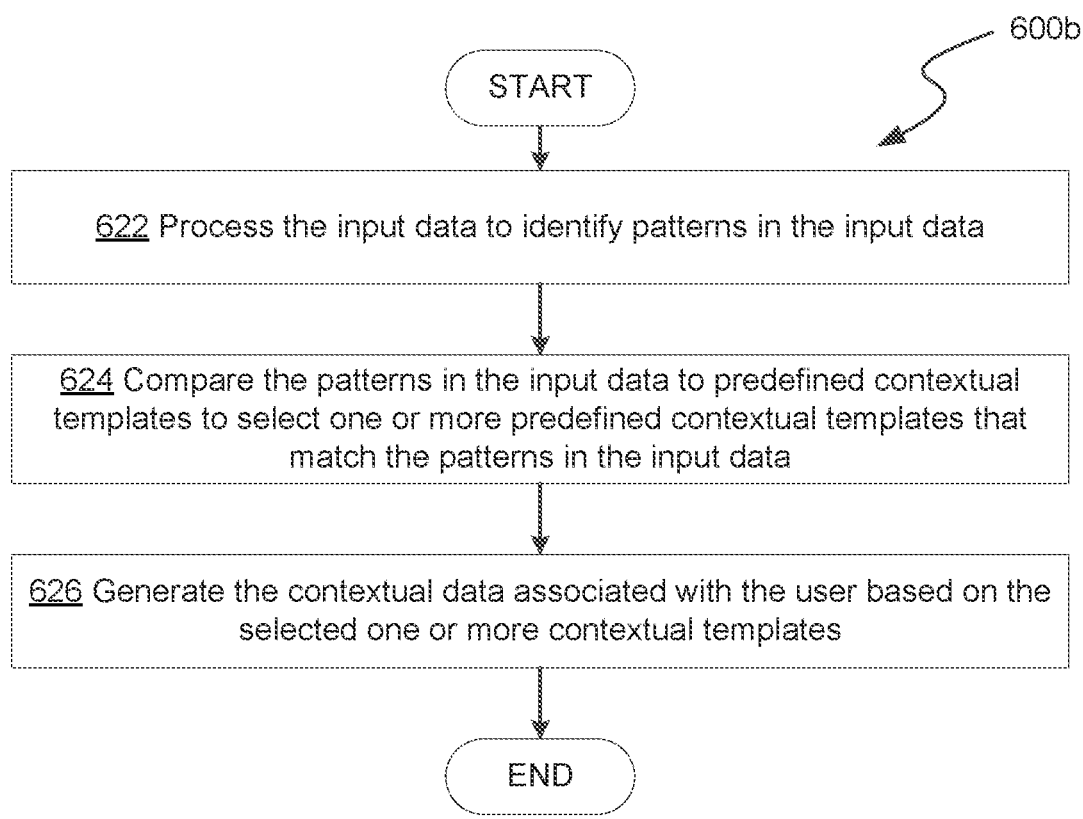
FIG. 6B shows a flow diagram of an example process for generating contextual data based on input data from various data sources

FIG. 6B shows a flow diagram of an example process 600b for generating contextual data based on input data from various data sources. In some embodiments, the example process 600b may be a subprocess of operation 606 of example process 600a described with respect to FIG. 6A.

Example process 600b begins at operation 622 with processing the input data (e.g., input data received at operation 604 of example process 600a) to identify patterns in the input data. As previously discussed with respect to FIG. 4, the input data may be received from multiple different types of data sources. Accordingly, the input data may not conform to one type of format, labeling scheme, etc. In some embodiments, operation 622 may include a pre-processing step to clean up, filter, augment, or otherwise transform the data into a format suitable for further processing. For example, operation 622 may include pre-processing the input data as part of an extract, transform, and load (ETL) process before processing the data to identify patterns in the input data. Operation 622 may be performed in real time or near real time (i.e., within seconds or fractions of a second) in response to receiving the input data.

Patterns identified in the input data may be based on various factors such as temporal proximity, spatial proximity, related information, common devices, etc. For example, operation 622 may include processing input data to identify a particular pattern based on a combination of location data 406 (i.e., indicative of a location of a user) and related fitness data 410 (e.g., indicative of a current activity of a user while at the location). As another example, operation 622 may include processing input data to identify a particular pattern based on a combination of user input data 404 (e.g., a photo) and social medial data 408 (e.g., that was posted in close temporal proximity to the photo). In some embodiments, the input data may be processed using one or more machine learning models (e.g., decision trees, Naïve Bayes classifiers, support vector machines, random forests, artificial neural networks, etc.) to identify patterns in the input data. Such models may be trained based on input data from multiple other users to identify one or more particular patterns in the input data.

Example process 600b continues at operation 624 with comparing the patterns in the input data to predefined contextual templates to select one or more predefined contextual templates that match the patterns. For example, in some embodiments, the health management platform 102 may include a database of predefined contextual templates that represent various contexts such as a particular chronic health condition, a particular health state, a particular location, a particular activity, etc. Each predefined contextual template may be associated with specified patterns of data. For example, a contextual template indicative of being at home may be associated with various specified patterns of data such as a threshold proximity to a known residence location, a type of device used, a social media check in post indicative that the user is at home, etc. As another example, a predefined contextual template indicative of performance of an exercise activity may be associated with various specified patterns of data such as motion pattern from an accelerometer, a signal from an exercise device, a threshold proximity to a known gym location, etc. As another example, a predefined contextual template indicative of a particular chronic health condition such as diabetes may be associated with various specified patterns of data such as a range of values for a health measurement, a particular pattern of health measurement values over time, etc.

In some embodiments, the predefined contextual templates of may be generated based on inputs from health professionals or other experts. For example, one or more clinicians may provide input to generate predefined contextual templates indicative of certain chronic health conditions and/or health states. In some embodiments, contextual templates may be generated automatically using machine learning techniques. For example, a machine learning model may be trained, using motion data from multiple fitness devices, to identify patterns in the motion data associated with various activities (e.g., walking, running, swimming, etc.). These patterns identified using the training data may then be used to generate predefined contextual templates associated with such activities.

In some embodiments, predefined contextual templates that "match" the identified patterns in the input data may actually refer to predefined contextual templates that substantially match (i.e., within some degree of tolerance) even if they do not exactly match. For example, a particular pattern identified in the input data may represent a 95% match with a pattern of data associated with a predefined contextual template. In such a situation, the predefined contextual template may be selected as a match if the 95% match level satisfies a match criterion (e.g., is above a specified threshold such as 90% match). In some embodiments, the match criterion may be set by an individual that specified the predefined contextual template. Alternatively, or in addition, the match criterion may dynamically change over time, for example, using machine learning techniques. In some embodiments, each predefined contextual template is associated with its own match criterion.

Example process 600b concludes at operation 626 with generating contextual data associated with the user based on the selected matching predefine contextual templates. For example, if a pattern in the input data matches a predefined contextual template indicative of presence at home, then contextual data (i.e., that the user is at home) can be associated with the user. As another example, if a pattern in the input data matches a predefined contextual template indicative of a poor health state, then contextual data (i.e., that the user's health state is poor) can be associated with the user. In such embodiments, "generating" the contextual data may include, accessing the stored matching contextual templates and associating the matching contextual templates as contextual data. In other words, the contextual data may be the same or substantially similar to the contextual templates.

Figure 6C:
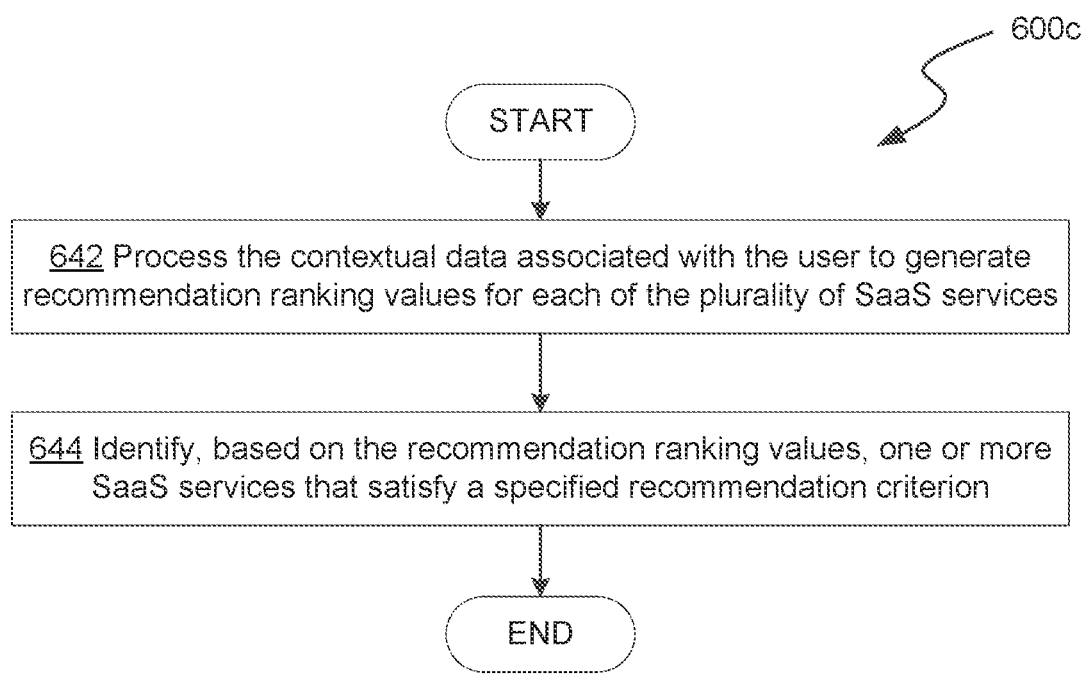
FIG. 6C shows a flow diagram of an example process for generating a recommendation based on the contextual data associated with a user

FIG. 6C shows a flow diagram of an example process 600c for generating a recommendation based on the contextual data associated with a user. In some embodiments, the example process 600c may be a subprocess of operation 608 of example process 600a described with respect to FIG. 6A.

Example process 600c beings at operation 642 with processing contextual data associated with a user to generate recommendation ranking values for various SaaS services provided by the health management platform 102. In some embodiments, the contextual data (e.g., one or more matching contextual templates) may be processed using a scoring engine that is configured to generate and output a recommendation ranking value associated with each SaaS service.

In some embodiments, the scoring engine may apply one or more deterministic rules to generate the recommendation ranking values. Alternatively, or in addition, the scoring engine may apply probabilistic machine learning techniques to generate the recommendation ranking values. Examples of techniques that can be applied by the scoring engine include decision trees, directed graphs (acyclical or not), Naïve Bayes classifiers, support vector machines, random forests, artificial neural networks, etc.

The recommendation ranking values generated by the scoring engine can include numerical values and or categorical values. Numerical values may include, for example, a value from 0 to 100 with 0 representing a lowest recommendation rank and 100 representing a highest recommendation rank. Categorical values may include values split into categories such as "not recommended," "neutral," and "recommended." These are just example recommendation ranking values and are not to be construed as limiting. The type of recommendation ranking value applied may depend on the type of scoring technique applied by the scoring engine.

Example process 600c continues at operation 644 with identifying, based on the recommendation ranking values, one or more of the SaaS services that satisfy a specified recommendation criterion. As specified recommendation criterion may be based, for example, on a specified threshold recommendation ranking value. For example, any SaaS service associated with a recommendation ranking value at or above the specified threshold may be identified as satisfying the specified recommendation ranking criterion. In some embodiments, the recommendation ranking criterion may be specified by a user (e.g., an administrative user) of the health management platform 102. In some embodiments, the recommendation ranking criterion may be automatically set and dynamically updated by a computer system associated with the health management platform 102. For example, in some embodiments, the recommendation ranking criterion may dynamically change in response to detected changes in the contextual data associated with the user.

Figure 6D:
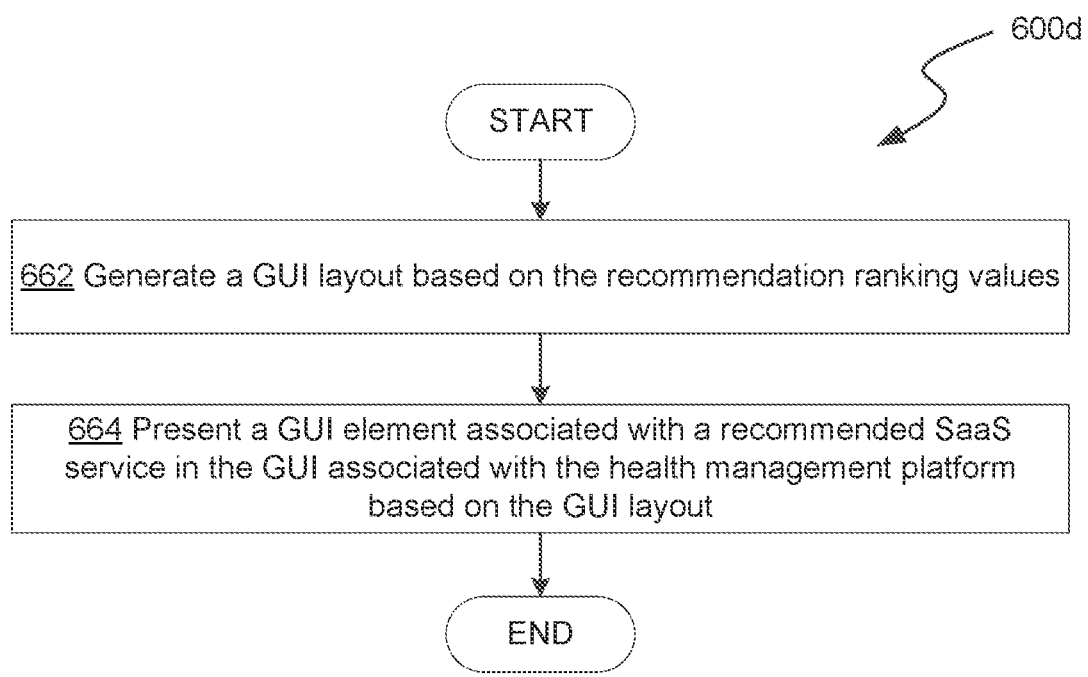
FIG. 6D shows a flow diagram of an example process for presenting a recommendation in a GUI of the health management platform.

FIG. 6D shows a flow diagram of an example process 600d for presenting a recommendation in a GUI of the health management platform. In some embodiments, the example process 600d may be a subprocess of operation 610 of example process 600a described with respect to FIG. 6A.

Example process 600d begins at operation 662 with generating a GUI layout based on recommendation ranking values (e.g., the recommendation ranking values generated at operation 642 of example process 600c) associated with the multiple SaaS services of the health management platform 102. An example GUI layout is shown in FIG. 6E, which is described in more detail below.

Example process 600d concludes at operation 664 with presenting interactive elements associated with one or more recommended SaaS services in the GUI (e.g., interface 104) associated with the health management platform 102. Examples of interactive elements presented in a GUI are shown in FIGS. 7-9, which are described in more detail below.

Figure 6E:
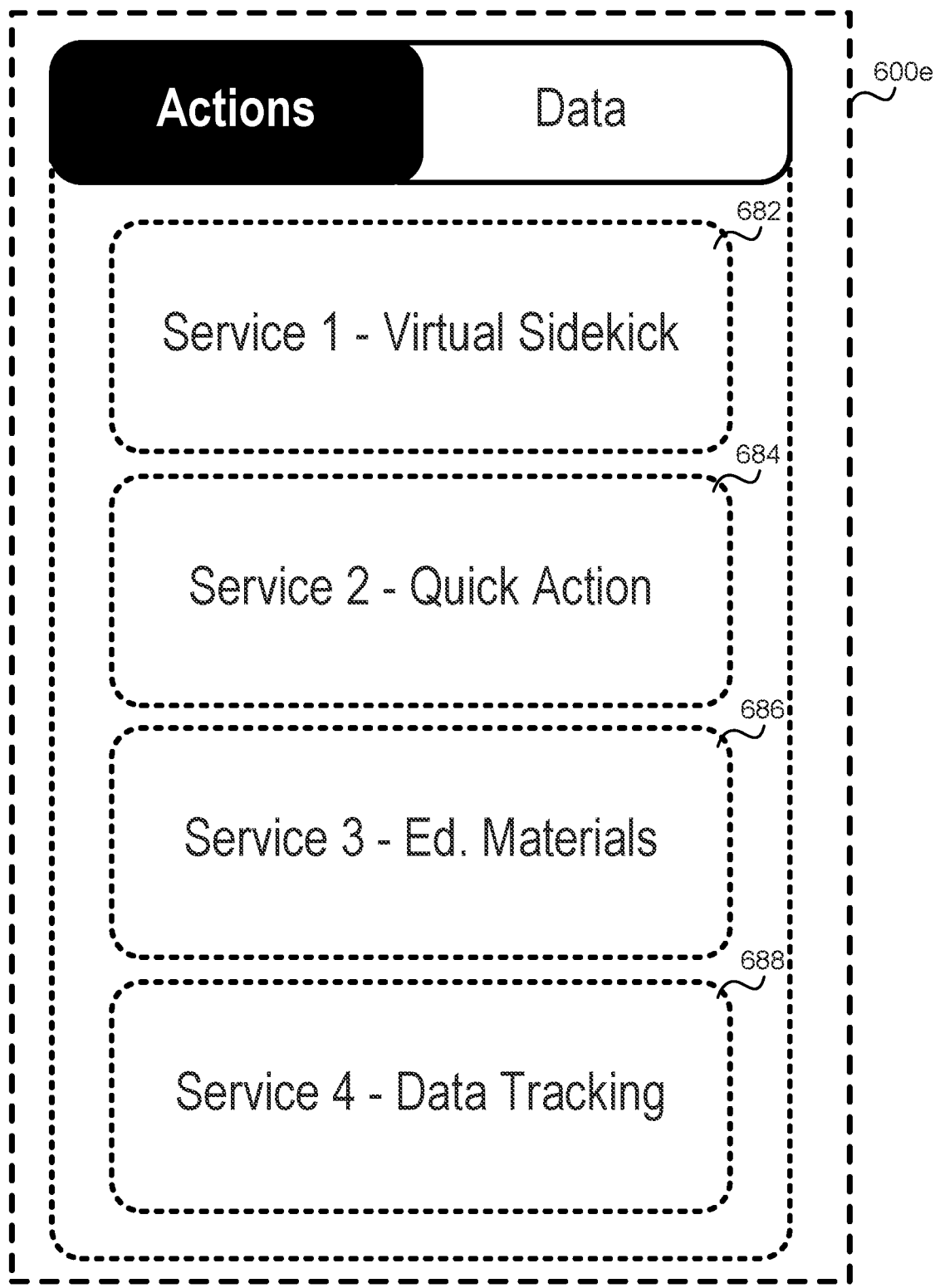
FIG. 6E shows a representation of an example GUI layout that may be generated base on recommendation ranking values associated with the multiple services of the health management platform.

FIG. 6E shows a representation of an example GUI layout 600e that may be generated base on recommendation ranking values associated with the multiple SaaS services of the health management platform 102. As shown in FIG. 6E, the example GUI layout 600e includes an arrangement of GUI elements associated with various SaaS services of a health management platform 102. Specifically, the example GUI layout depicted in FIG. 6E shows a vertical arrangement of GUI elements including a first element 682 associated with a virtual sidekick service, a second element 684 associated with a quick action service, a third element 686 associated with an educational materials service, and a fourth element 688 associated with a data tracking service. In some embodiments, the elements are arranged in the layout based on their respective recommendation ranking values. For example, each of the multiple elements 682-688 may be associated with SaaS services that satisfy the specified recommendation ranking criterion; however, certain elements (e.g., element 682) may be associated with services that have higher recommendation ranking values than other services. In this example, an interactive element 682 is placed at the top of the example GUI layout 600e since it is associated with a highly recommended service (based on the contextual data associated with the user). The GUI layout depicted in FIG. 6E is an example provided for illustrative purposes and is not to be construed as limiting. Other embodiments may arrange GUI elements differently than as depicted in FIG. 6E.

The example GUI layout 600e shown in FIG. 6E may represent a generated layout at a particular point in time. In some embodiments, the GUI layout may dynamically change as the contextual data associated with the user changes. For example, in response to receiving updated input data, the system may dynamically update the contextual data associated with the user, for example, using process 600b. In response to changes in the contextual data associated with the user, the system may dynamically update the recommendation ranking values associated with the various SaaS services, for example, using process 600c. Operations 662 and 664 in example process 600d can then be performed again to dynamically update the GUI layout and to present interactive elements associated with SaaS services based on the updated GUI layout.

Example Graphical User Interface

FIGS. 7-9 shows example screens of an example GUI associated with a health management platform 102. The GUI may be part of an interface 104 associated with health management platform 102. As shown in FIGS. 7-9, the example screens depict various interface elements which may represent presented recommendations to a user. In some embodiments, interactive elements associated with recommended SaaS services are presented in a GUI using a GUI layout (e.g., as described with respect to FIG. 6E) that is generated based on recommendation ranking values associated with the various SaaS services.

FIG. 7 shows example screens 702a and 702b of an example GUI that depict various interactive interface elements which may represent presented recommendations to a user to access quick action and/or challenge services of the health management platform 102.

Specifically, element 704 includes a recommendation to the user to access a challenges service of the health management platform 102. This element 704 may be automatically presented in the GUI as a recommendation based on generated contextual data associated with the user. In the example depicted in FIG. 7, the challenge is an exercise challenge (e.g., walk 1 mile every day for a week); however, other such challenges may similarly be presented via the GUI. Other challenges may include, for example, food swap challenges to swap certain food items for healthier options (e.g., high sugar vs. low sugar, high carb vs. low carb, etc.), educational challenges to learn about more about certain chronic health conditions and effective techniques for managing such conditions, etc. In response to the user interacting with element 704, the health management platform 102 may initiate an exercise challenge for the user. The exercise challenge as a service may include presenting recommended quick actions such as specific exercises, presenting recommended educational materials, presenting motivational messages to the user, tracking fitness data, presenting analysis of the fitness data, etc.

Elements 706, 708, and 710 are interactive elements for the user to perform one or more recommended quick actions. The elements 706, 708, and 710 may be automatically presented in the GUI as recommendations based on generated contextual data associated with the user. For example, the contextual data may indicate that the user is diabetic, has not yet had dinner, etc. By interacting with the quick action elements, the user may perform one or more of the recommended quick actions. For example, by interacting with element 706 the user can perform a quick action to input what they are having for dinner, for example, by taking a picture of their dinner, selecting from one or more predefined options presented via the GUI, or participating in an audio-based natural language conversation with a virtual assistant. For example, in response to the user selecting element 706, the virtual assistant may initiate an audio-based patient survey conversation to inquire about what the user is planning on eating for dinner and, if necessary, make some suggestions for healthier alternatives.

FIG. 8 shows an example screen 802 of an example GUI that depicts various interface elements which may represent presented recommendations to a user to access educational services of the health management platform 102.

Specifically, element 804 is an interactive element for accessing a guide on eating well. In response to a user interacting with element 804, one or more media (e.g., text-based articles, audio, video, images, etc.) associated with the guide may be presented to the user. Similarly, element 806 is an interactive element for accessing educational materials on how diet impacts blood glucose level. The elements 804 and 806 may be automatically presented in the GUI based on generated contextual data associated with the user (e.g., that the user is diabetic and is not effectively maintaining health blood glucose levels).

Elements 806, 808, and 810 are interactive elements for accessing additional information on upcoming events occurring in proximity to the user's physical location. For example, element 806 represents a presented recommendation to attend a free fitness event while element 810 represents a presented recommendation to attend a diabetes support group. Again, such elements may be automatically presented in the GUI based on contextual data associated with the user (e.g., that the user is diabetic and located at a particular physical location).

FIG. 9 shows example screens 902a-b of an example GUI that depicts various interface elements which may represent presented recommendations to a user to access data tracking and/or analytics services of the health management platform 102.

As shown in FIG. 9, the example screens 902a-b depict various visual elements based on obtained patient data (e.g., physiological and/or fitness data). Specifically, element 904 indicates a number of blood glucose readings within a goal range, element 906 depicts a listing of the blood glucose readings including those out of range, element 908 depicts a chart of blood glucose readings over the past day and in relation to events such as meals and tracked exercise, and element 910 depicts a listing of blood pressure readings from a blood pressure monitor. One or more of the elements 904-910 may be automatically presented in the GUI based on contextual data associated with the user (e.g., that the user has diabetes and recently ate).

The GUI screens depicted in FIGS. 7-9 are examples provided for illustrative purposes and are not to be construed as limiting. Other embodiments may include more of fewer interactive elements, may include different types of interactive elements, or may arrange the elements differently than as depicted while remaining within the scope of the disclosed technique.

Computer System

Figure 10:
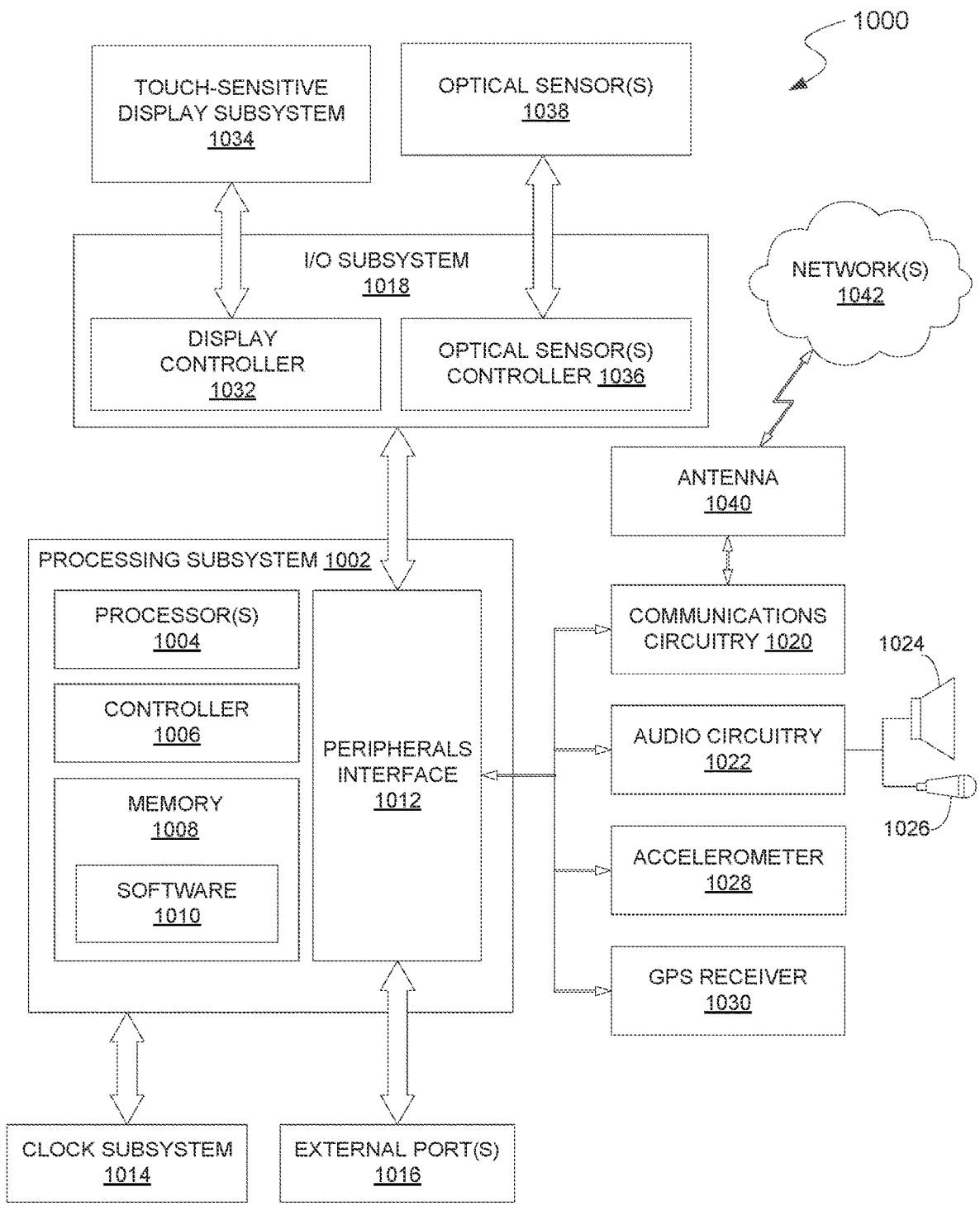
FIG. 10 shows a block diagram of an example computer system in which aspects of the disclosed technique can be implemented.

FIG. 10 is a block diagram illustrating an example computer system 1000 in which aspects of the disclosed technique can be implemented. In some embodiments, the computer system 1000 may represent or be a part of a user computing device (e.g., a smartphone) through which a user may access certain functionalities of a health management platform (e.g., health management platform 102). In some embodiments, computer system 1000 may represent or be a part of one or more computer devices that host the health management platform. The computer system 1000 may include generic components and/or components specifically designed to implement the disclosed technique. The computer system 1000 may be a standalone device or part of a distributed system that spans multiple networks, locations, machines, or combinations thereof. For example, components of the computer system 1000 may be included in or coupled to a system-on-chip (SOC), a single-board computer (SBC) system, a desktop or laptop computer, a smartphone, a kiosk, a mainframe, a mesh of computer systems, or combinations thereof.

In some embodiments, the computer system 1000 can operate as a server device or a client device in a client-server network environment, or as a peer machine in a peer-to-peer system. In some embodiments, the computer system 1000 may perform one or more steps of the disclosed embodiments in real-time, near real-time, offline, by batch processing, or combinations thereof.

The computer system 1000 includes a processing subsystem 1002 that includes one or more processors 1004 (e.g., central processing units (CPUs), graphical processing units (GPUs), application specific integrated circuits (ASICs), and/or field programmable gate arrays (FPGAs)), a memory controller 1006, memory 1008 that can store software 1010, and a peripherals interface 1012. The memory 1008 may include volatile memory (e.g., random-access memory (RAM)) and/or non-volatile memory (e.g., read-only memory (ROM)). The memory 1008 can be local, remote, or distributed. In some embodiments, memory 1008 may also include a data storage device such as a hard disk drive (HDD), a solid state drive (SSD), a removable drive (e.g., compact disc (CD)), etc. Memory 1008 may sometimes be referred to as a "computer-readable medium," a "machine-readable medium," and/or a "storage medium." While the memory 1408 is shown to be a single medium, the terms "computer-readable medium," "machine-readable medium," and "storage medium" should be taken to include a single medium or multiple media (e.g., a centralized/distributed database and/or associated caches and servers) that store one or more modules of software including one or more sets of instructions that are executable by the processors 1004.

The computer system 1000 can also include a clock subsystem 1014 that controls a timer for use in some embodiments. The components of the computer system 1000 are interconnected over a bus (not shown) operable to transfer data between hardware components. The bus can include a system bus, a Peripheral Component Interconnect (PCI) bus or PCI-Express bus, a HyperTransport or industry standard architecture (ISA) bus, a small computer system interface (SCSI) bus, a universal serial bus (USB), an IIC (I2C) bus, or an Institute of Electrical and Electronics Engineers (IEEE) standard 1394 bus (also referred to as "Firewire"), or any other appropriate bus for data transfer between components.

The peripherals interface 1012 is coupled to one or more external ports 1016 which can connect to an external power source, for example. The peripherals interface 1012 is also coupled to an I/O subsystem 1018. Other components coupled to the peripherals interface 1012 include communications circuitry 1020, audio circuitry 1022 for a speaker 1024 and a microphone 1026, an accelerometer 1028, a GPS receiver 1030 (or global navigation satellite system (GLONASS) or other global navigation system receiver), and other sensors (not shown). The GPS receiver 1030 is operable to receive signals concerning the geographic location of the computer system 1000. The accelerometer 1028 can be operable to obtain information concerning an orientation of the computer system 1400.

The I/O subsystem 1018 includes a display controller 1032 operative to control a touch-sensitive display system 1034, which further includes the touch-sensitive display of the computer system 1000. The I/O subsystem 1018 also includes an optical sensor(s) controller 1036 for one or more optical sensors 1038 of the computer system 1000. The I/O subsystem 1018 includes other components (not shown) to control physical buttons.

The communications circuitry 1020 may be part of a network adapter that enables the computer system 1000 to mediate data over networks 1042 (e.g., networks 106a-b of FIG. 1) with an entity that is external to the computer system 1400 through any communication protocol supported by the computer system 1000 and the external entity. The communications circuitry 1020 can include a network adaptor card, a wireless network interface card, a router, an access point, a wireless router, a switch, a multilayer switch, a protocol converter, a gateway, a bridge, a bridge router, a hub, a digital media receiver, a repeater, or any other components for wired or wireless communication with another entity over networks 1042.

In some embodiments, the communications circuitry 1020 can configure an antenna 1040 of the computer system 1000. In some embodiments, the antenna 1040 is structurally integrated with the computer system 1000 (e.g., embedded in the housing or display screen) or coupled to the computer system 1000 through the external ports 1016. The communications circuitry 1020 can convert electrical signals to/from electromagnetic signals that are communicated by the antenna 1040 to networks 1042 (e.g., networks 106a-b of FIG. 1) or other devices. For example, the communications circuitry 1020 can include radio frequency (RF) circuitry that processes RF signals communicated by the antenna 1040.

The communications circuitry 1020 can include circuitry for performing well-known functions such as an RF transceiver, one or more amplifiers, a tuner, oscillators, a digital signal processor, a codec chipset, a subscriber identity module (SIM card or eSIM), and so forth. The communications circuitry 1020 may communicate wirelessly via the antenna 1040 with the networks 1042 (e.g., the Internet, an intranet and/or a wireless network, such as a cellular network, a wireless local area network (LAN) and/or a metropolitan area network (MAN)) or other devices.

The software 1010 can include an operating system (OS) software program, application software programs, and/or other software modules (e.g., communication module 304, GUI module 306, processing module 308, services modules 309, recommendation module 310, storage modules 312 of FIG. 3). A software program, when referred to as "implemented in a computer-readable storage medium," includes computer-readable instructions stored in the memory (e.g., memory 1008). A processor (e.g., processor 1004) is "configured to execute a software program" when at least one value associated with the software program is stored in a register that is readable by the processor. In some embodiments, routines executed to implement the disclosed embodiments may be implemented as part of OS software (e.g., Microsoft Windows and Linux) or a specific software application, component, program, object, module, or sequence of instructions referred to as "computer programs."

Computer programs typically comprise one or more instructions set at various times in various memory devices of the computer system 1000, which, when read and executed by the processor 1004, will cause the computer system 1000 to execute functions involving the disclosed embodiments (e.g., operations associated with the processes of FIG. 6). In some embodiments, a carrier containing the aforementioned computer program product is provided. The carrier is one of an electronic signal, an optical signal, a radio signal, or a non-transitory computer-readable storage medium (e.g., the memory 1008).

Operation of the memory 1008, such as a change in state from a binary one (1) to a binary zero (0) (or vice versa) may comprise a visually perceptible physical change or transformation. The transformation may include a physical transformation of an article to a different state or thing. For example, a change in state may involve accumulation and storage of charge or a release of stored charge. Likewise, a change of state may comprise a physical change or transformation in magnetic orientation or a physical change or transformation in molecular structure, such as a change from crystalline to amorphous or vice versa.

Aspects of the disclosed embodiments may be described in terms of algorithms and symbolic representations of operations on data bits stored in memory. These algorithmic descriptions and symbolic representations generally include a sequence of operations leading to a desired result. The operations require physical manipulations of physical quantities. Usually, though not necessarily, these quantities take the form of electric or magnetic signals that are capable of being stored, transferred, combined, compared, and otherwise manipulated. Customarily, and for convenience, these signals are referred to as bits, values, elements, symbols, characters, terms, numbers, or the like. These and similar terms are associated with physical quantities and are merely convenient labels applied to these quantities.

The computer system 1000 may include other components that are not shown or further discussed herein for the sake of brevity. One having ordinary skill in the art will understand any hardware and software that is included but not shown in FIG. 10. While embodiments have been described in the context of fully functioning computing devices, those skilled in the art will appreciate that the various embodiments are capable of being distributed as a program product in a variety of forms and that the disclosure applies equally, regardless of the particular type of machine or computer-readable media used to actually effect the embodiments.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following claims should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

What is claimed is:

1. A method comprising:
causing display of a graphical user interface (GUI) associated with a health management platform at a user computing device that is associated with a user,
wherein the health management platform provides a plurality of software as a service (SaaS) services that employ different approaches to assist users in managing a chronic health condition;
receiving input data from a plurality of data sources, the plurality of data sources including (i) the user computing device and (ii) a health monitoring device that is associated with the user;
processing the input data to identify patterns in the input data;
comparing the patterns in the input data to a plurality of predefined contextual templates, each of which corresponds to a different health state of the chronic health condition, to select one or more predefined contextual templates that match the patterns in the input data;
generating contextual data that is indicative of a characterization of a current health state of the user by applying one or more rules to the selected one or more contextual templates;
processing, using a decision engine, the contextual data associated with the user to generate recommendation ranking values for each of the plurality of SaaS services,
wherein the recommendation ranking values are indicative of likelihood of the plurality of SaaS services successfully improving health of the user with respect to the chronic health condition;
identifying, based on the recommendation ranking values, a first SaaS service of the plurality of SaaS services that satisfies a specified ranking criterion;
presenting, in the GUI, a first interactive element associated with the first SaaS service that prompts the user to perform a discrete action;
detecting an interaction, by the user, with the first interactive element presented in the GUI,
wherein through the interaction, the user provides information regarding performance of the discrete action; and
initiating the first SaaS service associated with the first interactive element, with the information being provided to the first SaaS service as input.

2. The method of claim 1, further comprising:
identifying, based on the recommendation ranking values, a second SaaS service of the plurality of SaaS services that satisfies the recommendation criterion; and
presenting, in the GUI, a second interactive element associated with the second SaaS service that prompts the user to perform a second discrete action.

3. The method of claim 1, wherein the first interactive element associated with the first SaaS service is presented in the GUI automatically in real time in response to processing the contextual data associated with the user.

4. The method of claim 1, wherein the plurality of SaaS services of the health management platform include two or more of:
interactive quick actions;
interactive curated challenges;
educational materials;
data tracking and/or analytics;
a virtual sidekick; and
a virtual assistant.

5. The method of claim 1, further comprising:
receiving updated input data from one or more of the plurality of data sources;
detecting a change in the contextual data associated with the user as the updated input data are received from the one or more of the plurality of data sources;
generating, in response to the detected change in the contextual data, updated recommendation ranking values for each of the plurality of SaaS services;
identifying, based on the updated recommendation ranking values, a second interactive element associated with a second SaaS service of the plurality of SaaS services that satisfies the specified recommendation criterion;
generating, based on the updated recommendation ranking values, an updated GUI layout; and
presenting, in the GUI, based on the updated GUI layout, a second interactive element associated with the second SaaS service that prompts the user to perform a second discrete action.

6. The method of claim 1, wherein identifying the first SaaS service includes:
identifying a predefined activity to improve the health state of the user;
determining, based on a recommendation ranking value associated with the first SaaS service, that the first SaaS service has a higher likelihood of causing the user to perform the predefined activity than one or more of the other plurality of SaaS services of the health management platform; and
determining that the first SaaS service satisfies the specified recommendation criterion in response to determining that the first SaaS service has a higher likelihood of causing the user to perform the predefined activity than one or more of the other plurality of SaaS services of the health management platform.

7. The method of claim 6, wherein the predefined activity includes any of:
using a health monitoring device to acquire updated physiological data;
performing a fitness activity; or
swapping a first food item for a second food item in a meal.

8. The method of claim 6, wherein the contextual data is further indicative of a physical location of the user and wherein identifying the first SaaS service further includes:
determining that the predefined activity can be performed by the user at or in proximity to the physical location of the user;
wherein determining that the first SaaS service satisfies the specified recommendation criterion is further in response to determining that the predefined activity can be performed by the user at or in proximity to the physical location of the user.

9. The method of claim 6, wherein the contextual data is further indicative of an activity performed by the user and wherein identifying the first SaaS service further includes:
determining that the predefined activity is related to the activity performed by the user;
wherein determining that the first SaaS service satisfies the specified recommendation criterion is further in response to determining that the predefined activity is related to the activity performed by the user.

10. The method of claim 9, wherein:
the activity performed by the user is eating a meal and the predefined activity is swapping a first food item in the meal for a second food item;
the activity performed by the user is exercising and the predefined activity is meeting an exercise goal; or
the activity performed by the user is using a health monitoring device to acquire updated physiological data and the predefined activity is entering the updated physiological data via the GUI.

11. The method of claim 1, wherein the input data includes any one or more of:
a user input received from the user computing device, the user input based on an interaction by the user with the GUI at the user computing device;
physiological data received from a health monitoring device;
fitness data received from a fitness tracking device;
sensor data received from a sensor device;
location data received from the user computing device; or
weather data received from an online weather service.

12. A computer system associated with a health management platform, the health management platform configured to provide a plurality of software as a service (SaaS) services that employ different approaches to assist a user in managing a chronic health condition, the computer system comprising:
a processor; and
a memory coupled to the processor, the memory including instructions, which when executed by the processor, cause the computer system to:
cause display of a graphical user interface (GUI) associated with the health management platform at a user computing device;
receive input data from a plurality of data sources;
process the input data to identify patterns in the input data;
compare the patterns in the input data to a plurality of predefined contextual templates that match the patterns in the input data;
generate, based on the selected one or more contextual templates, contextual data associated with the user;
process, using a decision engine, the contextual data associated with the user to generate recommendation ranking values for each of the plurality of SaaS services,
wherein the recommendation ranking values are indicative of likelihood of the plurality of SaaS services assisting the user in managing the chronic health condition;
identify, based on the recommendation ranking values, a first SaaS service of the plurality of SaaS services that satisfies a specified ranking criterion;
present, in the GUI, a first interactive element associated with the first SaaS service that prompts the user to perform a discrete action; and
cause the first SaaS service to be initiated, with information regarding performance of the discrete action, conveyed by the user via an interaction with the first interactive element, being provided to the first SaaS service as input.

13. The computer system of claim 12, wherein the memory includes further instructions, which when executed by the processor, cause the computer system to further:
receive updated input data from one or more of the plurality of data sources;
detect a change in the contextual data associated with the user as the updated input data are received from the one or more of the plurality of data sources;
generate, in response to the detected change in the contextual data, updated recommendation ranking values for each of the plurality of SaaS services;
identify, based on the updated recommendation ranking values, a second interactive element associated with a second SaaS service of the plurality of SaaS services that satisfies the specified recommendation criterion; and
present, in the GUI, a second interactive element associated with the second SaaS service that prompts the user to perform a second discrete action.

14. The computer system of claim 12, wherein the contextual data is indicative of a health state of the user and wherein identifying the first SaaS service includes:
identifying a predefined activity to improve the health state of the user; and
determining, based on a recommendation ranking value associated with the first SaaS service, that the first SaaS service has a higher likelihood of causing the user to perform the predefined activity than one or more of the other plurality of SaaS services of the health management platform; and
determining that the first SaaS service satisfies the specified recommendation criterion in response to determining that the first SaaS service has a higher likelihood of causing the user to perform the predefined activity than one or more of the other plurality of SaaS services of the health management platform;
wherein the predefined activity includes any of:
using a health monitoring device to acquire updated physiological data;
performing a fitness activity; or
swapping a first food item for a second food item in a meal.

15. A non-transitory computer-readable medium with instructions stored thereon that, when executed by a computer system, cause the computer system to perform operations comprising:
causing display of a graphical user interface (GUI) associated with the health management platform at a user computing device that is associated with a user,
wherein the health management platform provides a plurality of software as a service (SaaS) services that are configured to assist users in managing a chronic health condition in different ways;
receiving input data from a plurality of data sources;
processing the input data to identify patterns in the input data;
comparing the patterns in the input data to a plurality of predefined contextual templates to select one or more predefined contextual templates that match the patterns in the input data;
determining, based on the selected one or more contextual templates, contextual data associated with the user of the health management platform;
processing, using a decision engine, the contextual data associated with the user to generate recommendation ranking values for each of the plurality of SaaS services,
wherein the recommendation ranking values are indicative of likelihood of the plurality of SaaS services assisting the user in managing the chronic health condition;

identifying, based on the recommendation ranking values, a first SaaS service of the plurality of SaaS services that satisfies a specified ranking criterion;

presenting, in the GUI, a first interactive element associated with the first SaaS service that prompts the user to perform a discrete action; and causing the first SaaS service to be initiated, with information regarding performance of the discrete action, conveyed by the user via an interaction with the first interactive element, being provided to the first SaaS service as input.

16. The non-transitory computer readable medium of claim 15, including further instructions, which when executed by the computer system, cause the computer system to perform operations further comprising:

detecting the interaction with the first interactive element presented in the GUI; and wherein said causing is performed in response to said detecting.

17. The non-transitory computer readable medium of claim 15, including further instructions, which when executed by the computer system, cause the computer system to perform operations further comprising:

receiving updated input data from one or more of the plurality of data sources;

detecting a change in the contextual data associated with the user as the updated input data are received from the one or more of the plurality of data sources;

generating, in response to the detected change in the contextual data, updated recommendation ranking values for each of the plurality of SaaS services;

identifying, based on the updated recommendation ranking values, a second interactive element associated with a second SaaS service of the plurality of SaaS services that satisfies the specified recommendation criterion; and presenting, in the GUI, a second interactive element associated with the second SaaS service that prompts the user to perform a second discrete action.

18. A method performed by a computer program that executes on a computing device associated with a user known to have a chronic health condition and offers a plurality of software as a service (SaaS) services that employ different approaches to manage the chronic health condition, the method comprising:

receiving data regarding digital and physical activities performed by the user from a plurality of sources, wherein the plurality of sources includes (i) at least one computer program executing on the computing device and (ii) a health monitoring device that is associated with the user;

processing the data to identify a pattern;

comparing the pattern to a plurality of predefined contextual templates, each of which corresponds to a different context, to select a predefined contextual template that matches the pattern identified in the data;

generating, based on the predefined contextual template, contextual data for the user;

processing the contextual data to generate recommendation ranking values for the plurality of SaaS services, wherein each of the recommendation ranking values is indicative of a likelihood of a corresponding one of the plurality of SaaS services successfully improving health of the user with respect to the chronic health condition;

identifying, based on the recommendation ranking values, a SaaS service from among the plurality of SaaS services that satisfies a ranking criterion;

causing digital presentation of a graphical user interface that includes an interactive element that is associated with the SaaS service and prompts the user to perform a discrete action;

detecting an interaction, by the user, with the interactive element presented in the graphical user interface, wherein through the interaction, the user provides information regarding performance of the discrete action; and initiating the SaaS service, with the information being provided to the SaaS service as input.

19. The method of claim 18, wherein the interactive element includes a button, an editable field, a checkbox, a radio button, an interactive list, a toggle, or any combination thereof.

20. The method of claim 18, wherein said generating comprises:

applying a rule to the predefined contextual template, so as to produce an output that indicates whether the pattern is indicative of a normal context for the user.

21. The method of claim 18, wherein said generating comprises:

processing the pattern identified in the data using a machine learning model that infers whether the pattern is indicative of a normal context for the user.

* * * * *